(12) United States Patent
Augustyns et al.

(10) Patent No.: US 10,738,002 B2
(45) Date of Patent: Aug. 11, 2020

(54) HALOGENATED BENZOTROPOLONES AS ATG4B INHIBITORS

(71) Applicants: Universiteit Antwerpen, Antwerp (BE); Universitair Ziekenhuis Antwerpen, Edegem (BE)

(72) Inventors: Koen Augustyns, Antwerp (BE); Matthias Cleenewerck, Antwerp (BE); Guido R. Y. De Meyer, Antwerp (BE); Jurgen Joossens, Antwerp (BE); Ammar Kurdi, Antwerp (BE); Pieter Van Der Veken, Antwerp (BE); Christel Vangestel, Edegem (BE); Sigrid Stroobants, Edegem (BE); Wim Martinet, Antwerp (BE)

(73) Assignees: UNIVERSITAIR ZIEKENHUIS ANTWERPEN, Edegem (BE); UNIVERSITEIT ANTWERPEN, Antwerp (BE)

( * ) Notice: Subject to any disclaimer, the term of this patent is extended or adjusted under 35 U.S.C. 154(b) by 0 days.

(21) Appl. No.: 16/463,544

(22) PCT Filed: Nov. 24, 2017

(86) PCT No.: PCT/EP2017/080319
§ 371 (c)(1),
(2) Date: May 23, 2019

(87) PCT Pub. No.: WO2018/096088
PCT Pub. Date: May 31, 2018

(65) Prior Publication Data
US 2019/0284130 A1    Sep. 19, 2019

(30) Foreign Application Priority Data
Nov. 24, 2016  (EP) .................................. 16200563

(51) Int. Cl.
| | | |
|---|---|---|
| C07C 235/82 | (2006.01) |
| C07C 62/38 | (2006.01) |
| C07C 69/757 | (2006.01) |
| A61P 35/00 | (2006.01) |

(52) U.S. Cl.
CPC ............ *C07C 235/82* (2013.01); *A61P 35/00* (2018.01); *C07C 62/38* (2013.01); *C07C 69/757* (2013.01); *C07C 2602/12* (2017.05)

(58) Field of Classification Search
CPC ... C07C 235/82; C07C 2602/12; C07C 62/38; C07C 69/757
See application file for complete search history.

(56) References Cited

U.S. PATENT DOCUMENTS

| | | |
|---|---|---|
| 4,997,834 A | 3/1991 | Muro et al. |
| 6,369,086 B1 | 4/2002 | Davis et al. |
| 6,369,087 B1 | 4/2002 | Whittle et al. |
| 6,372,733 B1 | 4/2002 | Caldwell et al. |
| 6,372,778 B1 | 4/2002 | Tung et al. |
| 2011/0123468 A1* | 5/2011 | Wagner ................... A61P 39/06 424/59 |

FOREIGN PATENT DOCUMENTS

| | | |
|---|---|---|
| EP | 0370498 A2 | 11/1989 |
| EP | 0721331 B1 | 9/1994 |
| RU | 2359954 | * 10/2008 |
| WO | 2005021479 A1 | 3/2005 |
| WO | WO2014/022287 | * 2/2014 |

OTHER PUBLICATIONS

International Search Report dated Feb. 13, 2018, in reference to co-pending European Patent Application No. PCT/EP2017/080319 filed Nov. 24, 2017.
Extended European Search Report in reference to co-pending European Patent Application No. EP 16200563 filed Jun. 6, 2017.
Krupa S. Jani et al., "Computational design of targeted inhibitors of Polo-like Kinase 1 (Plk1)," Bioinformatics and Biology Insi, Libertas Academica Ltd, NZ, vol. 6, Jan. 1, 2012, pp. 23-31, XP008182637.
C.-W. Shu et al., "High-Throughput Fluorescence Assay for Small-Molecule Inhibitors of Autophagins/Atg4," Journal of Biomolecular Screening, vol. 16, No. 2, Jan. 18, 2011 (Jan. 18, 2011), pp. 174-182, XP055329745.
Chih-Wen Shu et al., "Synthetic substrates for measuring activity of autophagy proteases-autophagins (Atg4)", Autophagy, vol. 6, No. 7, Oct. 1, 2010 (Oct. 1, 2010), pp. 936-947, XP055158991.
Apel A, et al., "Blocked autophagy sensitizes resistant carcinoma cells to radiation therapy", Cancer Res. 2008, vol. 68 (5), pp. 1485-1494.
Akin D, et al. A novel ATG4B antagonist inhibits autophagy and has a negative impact on osteosarcoma tumors Autophagy 2014; vol. 10(11), pp. 2021-2035.

(Continued)

*Primary Examiner* — Valerie Rodriguez-Garcia
(74) *Attorney, Agent, or Firm* — Dinsmore & Shohl, LLP

(57) ABSTRACT

The present invention relates to compounds having a benzotropolone core, and compositions containing said compounds acting as ATG4B inhibitors, thereby inhibiting autophagy. Moreover, the present invention provides processes for the preparation of the disclosed compounds, as well as methods of using them, for instance as a medicine, in particular for the treatment of cell proliferative disorders, such as cancer. Halogenated benzotropolones described here are of formula

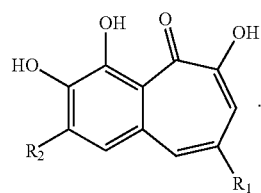

9 Claims, 2 Drawing Sheets

(56) References Cited

OTHER PUBLICATIONS

Rothe K, et al., "The core autophagy protein ATG4B is a potential biomarker and therapeutic target in CML stem/progenitor cells", Blood 2014; vol. 123(23), pp. 3622-3634.
Ketteler R, et al., "Quantitation of autophagy by luciferase release assay", Autophagy. 2008; vol. 4(6), pp. 801-806.
Li M, et al., "Kinetics Comparisons of Mammalian Atg4 Homologues Indicate Selective Preferences toward Diverse Atg8 Substrates", J Biol. Chem. 2011, vol. 286(9), pp. 7327-7338.
Stankov, et al., "Flow Cytometric Analysis of Autophagic Activity with Cyto-ID Staining in Primary Cells", Research Gate, vol. 4, Iss 7, Apr. 5, 2014.
Sugawara, et al., "Structural Basis for the Specificity and Catalysis of Human Atg4B Responsible for Mammalian Autophagy", The Journal of Biological Chemistry, vol. 280, No. 48, Dec. 2. 2005, pp. 40058-40065.

* cited by examiner

HALOGENATED BENZOTROPOLONES AS ATG4B INHIBITORS

CROSS-REFERENCES TO RELATED APPLICATIONS

This application is a national-stage application under 35 U.S.C. § 371 of International Application No. PCT/EP2017/080319, filed Nov. 24, 2017, which designates the United States and claims the benefit of priority to European Application No. 16200563.1, filed Nov. 24, 2016.

FIELD OF THE INVENTION

The present invention relates to compounds having a halogenated benzotropolone core, and compositions containing said compounds acting as Atg4B inhibitors, thereby inhibiting autophagy. Moreover, the present invention provides processes for the preparation of the disclosed compounds, as well as methods of using them, for instance as a medicine, in particular for the treatment of cell proliferative disorders, such as cancer.

BACKGROUND TO THE INVENTION

Autophagy is a catabolic cellular process by which double membranous vacuoles engulf and degrade cytoplasmic material. This constitutively active mechanism is crucial for the intracellular housekeeping of the cell. However, under stress conditions such as hypoxia, nutrient deprivation or DNA damage, autophagy is highly activated to restore energy production and promote survival. Activation of autophagy is therefore one of the strategies used by tumors in response to hypoxia and chemotherapy allowing it to survive the harsh microenvironment and to evade cell death. Indeed, pronounced accumulation of the autophagy marker microtubule-associated protein 1 (LC3B) is often predictive of poor prognosis in cancer patients. Following multiple preclinical studies reporting beneficial effects in tumor models upon autophagy inhibition, clinical trials featuring hydroxychloroquine were initiated to enhance the effectiveness of chemotherapy in patients. Hydroxychloroquine is a non-specific late autophagy inhibitor which abrogates the autophagosome-lysosome fusion, the last step of the autophagic flux. However, the drug is highly unspecific and can cause toxicity. A critical component of the autophagy machinery is the cysteine protease Atg4 (autophagy-related gene-4). Among the four distinct forms identified in mammals, only Atg4B has been shown to have an important role in autophagy (Li et al., 2011). The enzyme converts pro-LC3B to LC3B-I by cleaving its C-terminus after which LC3B-I can be conjugated to phosphatidylethanolamine by other Atgs, thereby forming LC3B-II. This lipidation process of LC3B-I allows expansion and closure of autophagosomes. Given the encouraging results following Atg4B inhibition in several tumors (Akin et al., 2014; Apel et al., 2008; Rothe et al., 2014), the enzyme is becoming increasingly attractive as a therapeutic target for cancer and considerable efforts have recently been made to identify small molecule Atg4B-inhibitors (Ketteler and Seed, 2008; Shu et al., 2010, 2011).

In the current invention, we disclose the discovery of novel autophagy inhibitors with a benzotropolone core structure. The benzotropolone scaffold is present in numerous known synthetic compounds and natural products and potential applications of benzotropolone-containing molecules are described in diverse fields. Examples include use as food stabilizers, antimicrobial agents, sunscreens, cosmetics and anti-obesity agents. However, this class of compounds was never investigated for autophagy modulation. In contrast, one benzotropolone was reported as a weak autophagy inhibitor by Shu et al. and was even reported as unattractive as a starting point for the development of potent and selective autophagy inhibitors. Furthermore, this compound showed no in cellulo autophagy inhibition. Moreover, in our hands, this compound did not show activity in a cellular screening assay for autophagy inhibitors.

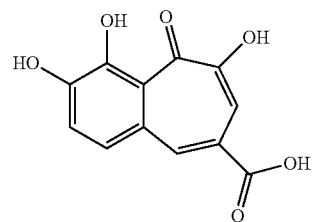

Benzotropolone, reported by Shu et al.

Therefore, surprisingly we have found potent in cellulo autophagy inhibition for a well-defined series of novel analogues of the reported molecule, which are characterized by having a halogen atom as specified in the claims. Furthermore, these halogenated analogues not only showed promising activity in living cells but also showed an improved stability in blood plasma and in the presence of liver microsomes.

While, the synthesis of one such halogenated benzotropolone compound has already been described in the early '60s (DE1091114, example 16), this type of compounds has not been further explored in the meantime, and its public disclosure is only limited to the synthesis route thereof, while no utility is described for that particular compound, or more generally the group of halogenated benzotropolones.

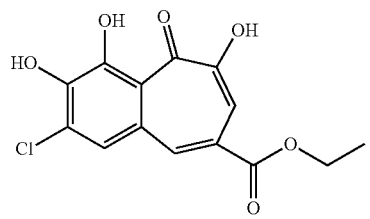

Halogenated Benzotropolone, as described in DE1091114

SUMMARY OF THE INVENTION

In a first aspect, the present invention provides a compound of Formula I or a stereoisomer, tautomer, racemic, metabolite, pro- or predrug, salt, hydrate, or solvate thereof,

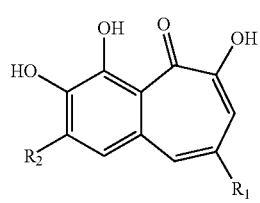

I

Wherein
R$_1$ is selected from —C$_{1-6}$ alkyl, —Ar$_1$, —(C=O)—O—R$_3$ and —(C=O)—NR$_4$R$_5$;
R$_2$ is -halo;
R$_3$ is selected from —H and —C$_{1-8}$ alkyl;
R$_4$ and R$_5$ are each independently selected from —H, —C$_{1-8}$ alkyl, —Ar$_2$ and -Het$_1$; wherein said —C$_{1-8}$alkyl is optionally substituted with one or more substituents selected from —Ar$_2$;
Ar$_1$ and Ar$_2$ are each independently a 5- to 10-membered aromatic cycle; wherein each of said —Ar$_1$ and —Ar$_2$ is optionally substituted with one or more substituents selected from; -halo, —C$_{1-6}$ alkyl, and —O—C$_{1-6}$ alkyl; wherein said —C$_{1-6}$ alkyl may be optionally substituted with from one to three -halo.
Het$_1$ is a 5- to 10-membered aromatic or non-aromatic heterocycle, optionally comprising 1 to 3 N, O or S atoms; wherein said Het$_1$ is optionally substituted with one or more substituents selected from -halo, —C$_{1-6}$ alkyl, —O—C$_{1-6}$ alkyl; wherein said —C$_{1-6}$ alkyl may be optionally substituted with from one to three -halo; and
wherein said compound is not

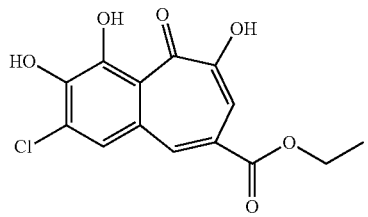 [SMILES: CCOC(=O)c1cc(O)c(=O)c2c(O)c(O)c(Cl)cc2c1]

In a particular embodiment, the present invention provides a compound of formula Ia;

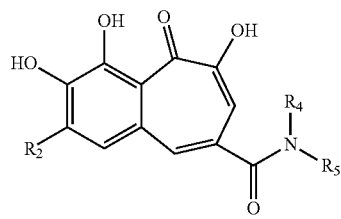

wherein
R$_2$ is -halo;
R$_4$ and R$_5$ are each independently selected from —H, —C$_{1-8}$ alkyl, —Ar$_2$ and -Het$_1$; wherein said —C$_{1-8}$alkyl is optionally substituted with one or more substituents selected from —Ar$_2$;
Ar$_2$ is a 5- to 10-membered aromatic cycle; wherein said —Ar$_2$ is optionally substituted with one or more substituents selected from; -halo, —C$_{1-6}$alkyl, and —O—C$_{1-6}$alkyl; wherein said —C$_{1-6}$alkyl may be optionally substituted with from one to three -halo.
Het$_1$ is a 5- to 10-membered aromatic or non-aromatic heterocycle, optionally comprising 1 to 3 N, O or S atoms; wherein said Het$_1$ is optionally substituted with one or more substituents selected from -halo, —C$_{1-6}$ alkyl, —O—C$_{1-6}$ alkyl; wherein said —C$_{1-6}$ alkyl may be optionally substituted with from one to three -halo.
In yet a further specific embodiment, the present invention provides a compound according to the current invention in which the following restrictions apply:

R$_2$ is -halo; and
R$_4$ and R$_5$ are each independently selected from —H, —C$_{1-8}$ alkyl and -phenyl.
In another embodiment, the present invention provides a compound of formula Ib;

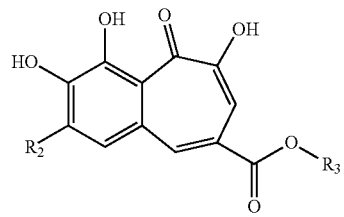

wherein
R$_2$ is -halo; and
R$_3$ is selected from —H and —C$_{1-8}$ alkyl; and
wherein said compound is not

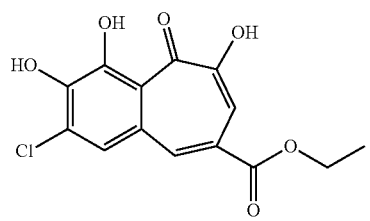 [SMILES: CCOC(=O)c1cc(O)c(=O)c2c(O)c(O)c(Cl)cc2c1]

In yet a further embodiment, the present invention provides a compound according to the present invention in which the following restrictions apply:
R$_1$ is —(C=O)—O—R$_3$;
R$_2$ is -halo; and
R$_3$ is selected from —H and —C$_{3-8}$ alkyl.
In another specific embodiment of the present invention R$_2$ is selected from the list comprising —Cl, —F, and —Br.
In a more specific embodiment, the present invention provides a compound selected from the list comprising:

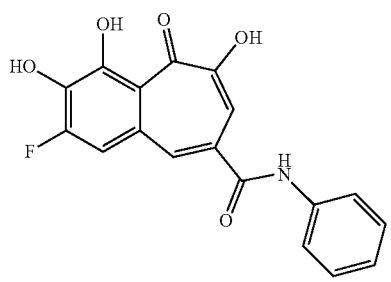

29

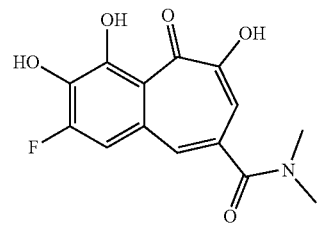

30

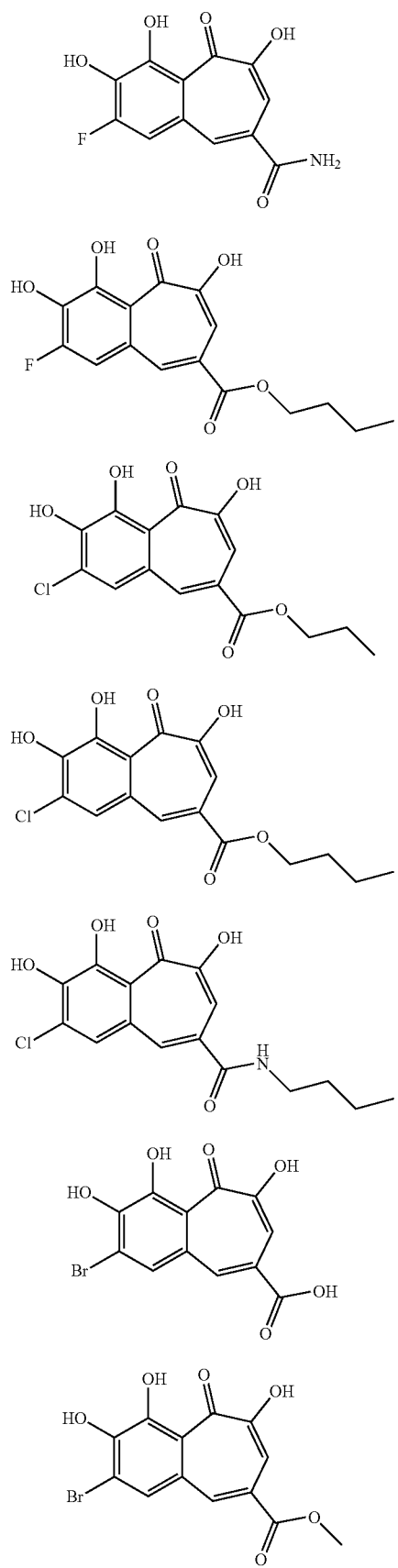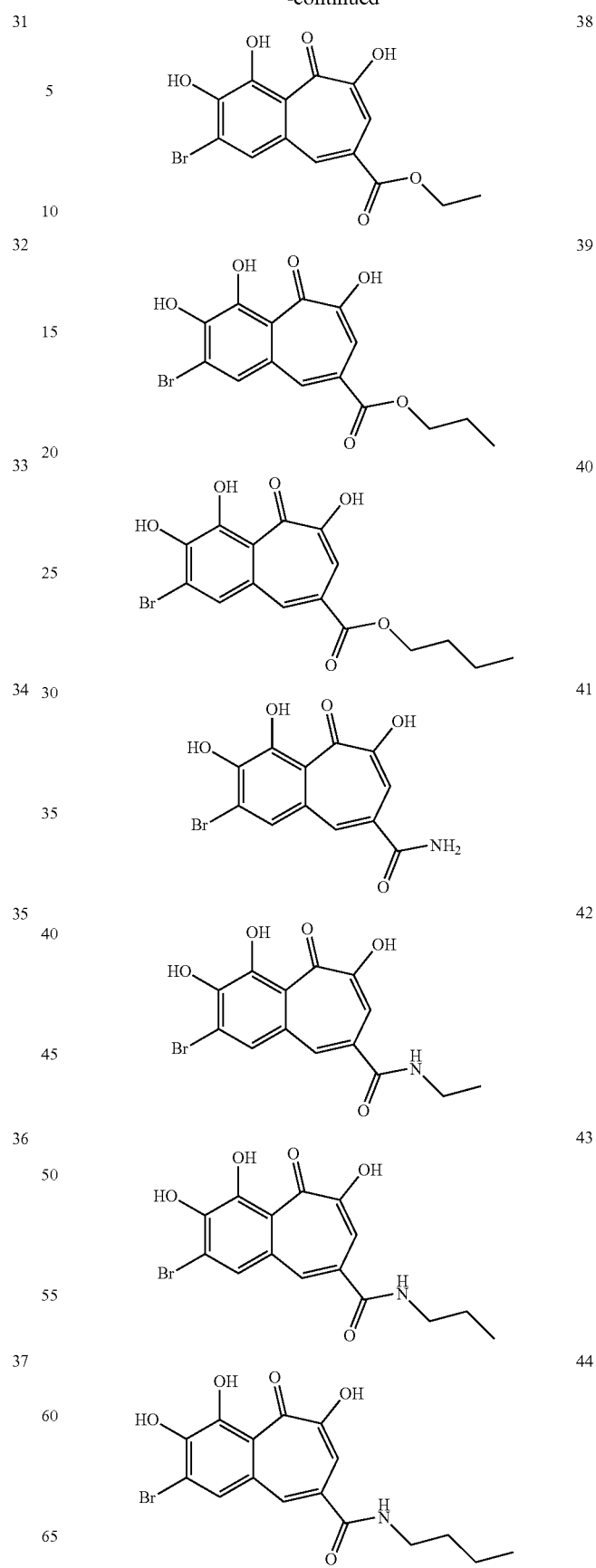

-continued

[Structure 45: benzocycloheptenone with OH, HO, OH, Br substituents and isopropyl amide]

[Structure 46: benzocycloheptenone with OH, HO, OH, Br substituents and benzyl amide]

[Structure 47: benzocycloheptenone with OH, HO, OH, Br substituents and isobutyl amide]

In a further aspect, the present invention provides a compound of Formula I or a stereoisomer, tautomer, racemic, metabolite, pro- or predrug, salt, hydrate, or solvate thereof,

[Structure I]

Wherein
$R_1$ is selected from —$C_{1-6}$ alkyl, —$Ar_1$, —(C=O)—O—$R_3$ and —(C=O)—$NR_4R_5$;
$R_2$ is -halo;
$R_3$ is selected from —H and —$C_{1-8}$ alkyl;
$R_4$ and $R_5$ are each independently selected from —H, —$C_{1-8}$ alkyl, —$Ar_2$ and -$Het_1$; wherein said —$C_{1-8}$alkyl is optionally substituted with one or more substituents selected from —$Ar_2$;
$Ar_1$ and $Ar_2$ are each independently a 5- to 10-membered aromatic cycle; wherein each of said —$Ar_1$ and —$Ar_2$ is optionally substituted with one or more substituents selected from; -halo, —$C_{1-6}$ alkyl, and —O—$C_{1-6}$ alkyl; wherein said —$C_{1-6}$ alkyl may be optionally substituted with from one to three -halo.
$Het_1$ is a 5- to 10-membered aromatic or non-aromatic heterocycle, optionally comprising 1 to 3 N, O or S atoms; wherein said $Het_1$ is optionally substituted with one or more substituents selected from -halo, —$C_{1-6}$ alkyl, —O—$C_{1-6}$ alkyl; wherein said —$C_{1-6}$ alkyl may be optionally substituted with from one to three -halo;
for use as a human or veterinary medicine.

In yet a further aspect, the present invention provides a compound of Formula I or a stereoisomer, tautomer, racemic, metabolite, pro- or predrug, salt, hydrate, or solvate thereof,

[Structure I]

Wherein
$R_1$ is selected from —$C_{1-6}$alkyl, —$Ar_1$, —(C=O)—O—$R_3$ and —(C=O)—$NR_4R_5$;
$R_2$ is -halo;
$R_3$ is selected from —H and —$C_{1-8}$ alkyl;
$R_4$ and $R_5$ are each independently selected from —H, —$C_{1-8}$ alkyl, —$Ar_2$ and -$Het_1$; wherein said —$C_{1-8}$alkyl is optionally substituted with one or more substituents selected from —$Ar_2$;
$Ar_1$ and $Ar_2$ are each independently a 5- to 10-membered aromatic cycle; wherein each of said —$Ar_1$ and —$Ar_2$ is optionally substituted with one or more substituents selected from; -halo, —$C_{1-6}$ alkyl, and —O—$C_{1-6}$ alkyl; wherein said —$C_{1-6}$ alkyl may be optionally substituted with from one to three -halo.
$Het_1$ is a 5- to 10-membered aromatic or non-aromatic heterocycle, optionally comprising 1 to 3 N, O or S atoms; wherein said $Het_1$ is optionally substituted with one or more substituents selected from -halo, —$C_{1-6}$ alkyl, —O—$C_{1-6}$ alkyl; wherein said —$C_{1-6}$ alkyl may be optionally substituted with from one to three -halo;
for use in the diagnosis, prevention and/or treatment of a cell proliferative disorder, such as cancer.

In a further aspect, the present invention provides the use of a compound as defined herein for inhibiting Atg4B activity.

The present invention also provides a pharmaceutical composition comprising a compound as defined herein.

In yet a further aspect, the present invention provides the use of a compound as defined herein or a pharmaceutical composition as defined herein, for the diagnosis, prevention and/or treatment of a cell proliferative disorder, such as cancer.

In a final aspect, the present invention provides a method for the prevention and/or treatment of a cell proliferative disorder, such as cancer; said method comprising administering to a subject in need thereof a therapeutically effective amount of a compound as defined herein, or a pharmaceutical composition as defined herein.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

DETAILED DESCRIPTION OF THE INVENTION

Figure 1:
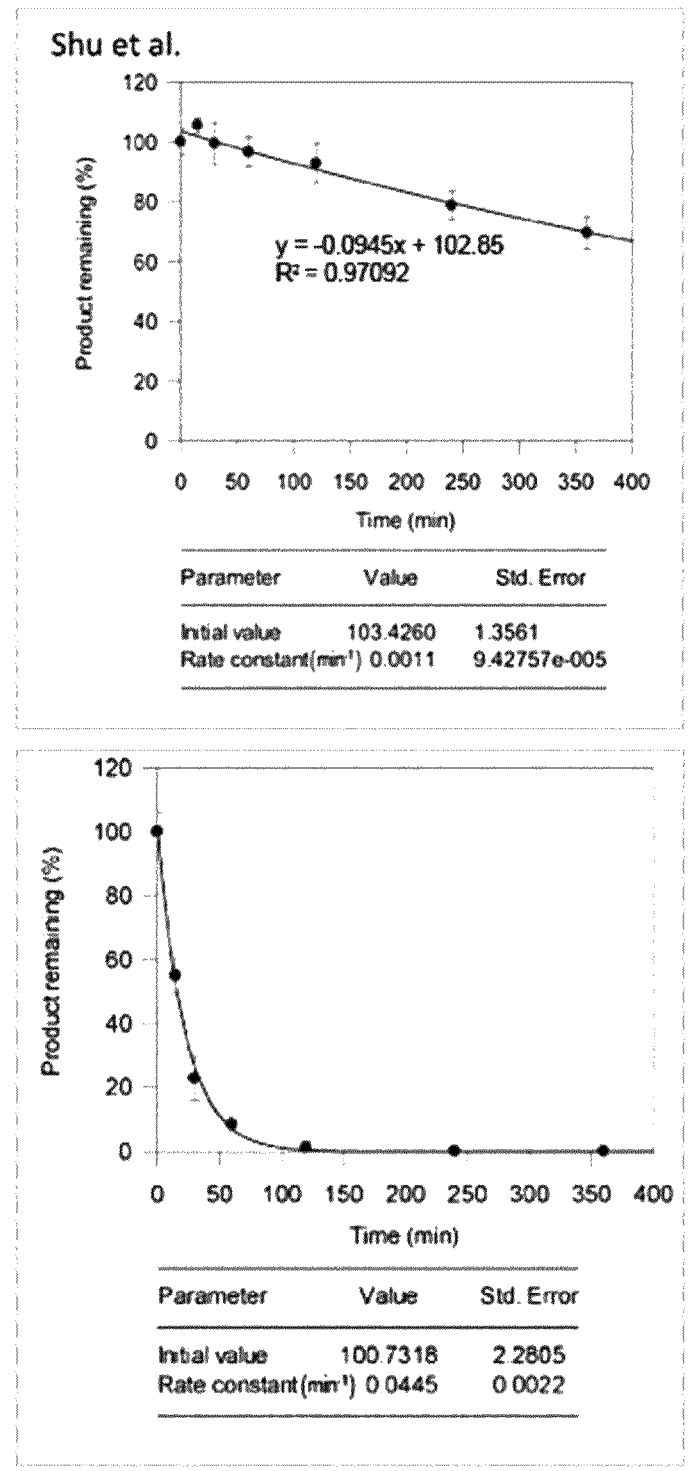
FIG. 1: Microsomal stability of reference compound (Shu et al.) and compound 40 in mouse plasma expressed as the % remaining product as a function of time. Error bars are the variation in duplicate measurements. Standard errors are the variations on the fitted curve.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Unless a context dictates otherwise, asterisks are used herein to indicate the point at which a mono- or bivalent radical depicted is connected to the structure to which it relates and of which the radical forms part.

As already mentioned hereinbefore, in a first aspect the present invention provides compounds of Formula I, or a stereoisomer, tautomer, racemic, metabolite, pro- or predrug, salt, hydrate, or solvate thereof,

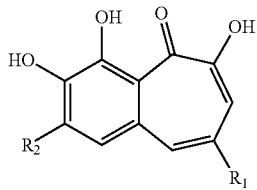

I

Wherein
$R_1$ is selected from $-C_{1-6}$ alkyl, $-Ar_1$, $-(C=O)-O-R_3$ and $-(C=O)-NR_4R_5$;
$R_2$ is -halo;
$R_3$ is selected from $-H$ and $-C_{1-8}$ alkyl;
$R_4$ and $R_5$ are each independently selected from $-H$, $-C_{1-8}$ alkyl, $-Ar_2$ and $-Het_1$; wherein said $-C_{1-8}$alkyl is optionally substituted with one or more substituents selected from $-Ar_2$;
$Ar_1$ and $Ar_2$ are each independently a 5- to 10-membered aromatic cycle; wherein each of said $-Ar_1$ and $-Ar_2$ is optionally substituted with one or more substituents selected from; -halo, $-C_{1-6}$ alkyl, and $-O-C_{1-6}$ alkyl; wherein said $-C_{1-6}$ alkyl may be optionally substituted with from one to three -halo.
$Het_1$ is a 5- to 10-membered aromatic or non-aromatic heterocycle, optionally comprising 1 to 3 N, O or S atoms;
wherein said $Het_1$ is optionally substituted with one or more substituents selected from -halo, $-C_{1-6}$ alkyl, $-O-C_{1-6}$ alkyl; wherein said $-C_{1-6}$ alkyl may be optionally substituted with from one to three -halo; and wherein said compound is not

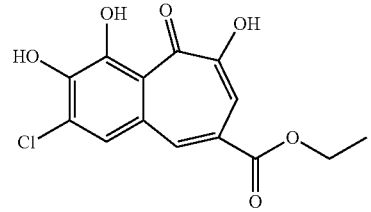 [SMILES: CCOC(=O)c1cc(O)c(=O)c2c(O)c(O)c(Cl)cc2c1]

When describing the compounds of the invention, the terms used are to be construed in accordance with the following definitions, unless a context dictates otherwise:

The term "alkyl" by itself or as part of another substituent refers to a fully saturated hydrocarbon of Formula $C_xH_{2x+1}$ wherein x is a number greater than or equal to 1. Generally, alkyl groups of this invention comprise from 1 to 8 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$alkyl means an alkyl of one to four carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers, heptyl and its isomers, octyl and its isomers, nonyl and its isomers; decyl and its isomers. $C_1$-$C_6$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopentyl, 2-, 3-, or 4-methylcyclopentyl, cyclopentylmethylene, and cyclohexyl.

The term "optionally substituted alkyl" refers to an alkyl group optionally substituted with one or more substituents (for example 1 to 4 substituents, for example 1, 2, 3, or 4 substituents or 1 to 2 substituents) at any available point of attachment. Non-limiting examples of such substituents include halo, hydroxyl, carbonyl, nitro, amino, oxime, imino, azido, hydrazino, cyano, aryl, heteroaryl, cycloalkyl, acyl, alkylamino, alkoxy, thiol, alkylthio, carboxylic acid, acylamino, alkyl esters, carbamate, thioamido, urea, sullfonamido and the like.

The terms "heterocyclyl", "heterocycle" or "heterocyclo" as used herein by itself or as part of another group refer to non-aromatic, fully saturated or partially unsaturated cyclic groups (for example, 3 to 13 member monocyclic, 7 to 17 member bicyclic, or 10 to 20 member tricyclic ring systems, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. An optionally substituted heterocyclic refers to a heterocyclic having optionally one or more substituents (for example 1 to 4 substituents, or for example 1, 2, 3 or 4), selected from those defined above for substituted aryl.

Exemplary heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, succinimidyl, 3H-indolyl, isoindolinyl, chromenyl, isochromanyl, xanthenyl, 2H-pyrrolyl, 1-pyrrolinyl, 2-pyrrolinyl, 3-pyrrolinyl, pyrrolidinyl, 4H-quinolizinyl, 4aH-carbazolyl, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro-2H-pyranyl, phthalazinyl, oxetanyl, thietanyl, 3-dioxolanyl, 1,3-dioxanyl, 2,5-dioximidazolidinyl, 2,2,4-piperidonyl, 2-oxopiperidinyl, 2-oxopyrrolodinyl, 2-oxoazepinyl, indolinyl, tetrahydropyranyl, tetrahydrofuranyl, tetrehydrothienyl, tetrahydroquinolinyl, tetrahydroisoquinolinyl, thiomorpholinyl, thiomorpholinyl sulfoxide, thiomorpholinyl sulfone, 1,3-dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro-1,1-dioxothienyl, N-formylpiperazinyl, and morpholinyl.

The term "aryl" or "aromatic cycle" as used herein refers to a polyunsaturated, aromatic hydrocarbyl group having a single ring (i.e. phenyl) or multiple aromatic rings fused together (e.g. naphthalene or anthracene) or linked covalently, typically containing 6 to 10 atoms; wherein at least one ring is aromatic. The aromatic ring may optionally include one to three additional rings (either cycloalkyl, heterocyclyl, or heteroaryl) fused thereto. Aryl also includes the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7-, or 8-azulenyl, 1- or 2-naphthyl, 1-, 2-, or 3-indenyl, 1-, 2-, or 9-anthryl, 1-2-, 3-, 4-, or 5-acenaphtylenyl, 3-, 4-, or 5-acenaphtenyl, 1-, 2-, 3-, 4-, or 10-phenanthryl, 1- or 2-pentalenyl, 1, 2-, 3-, or 4-fluorenyl, 4- or 5-indanyl, 5-, 6-, 7-, or 8-tetrahydronaphthyl, 1,2,3,4-tetrahydronaphthyl, 1,4-dihydronaphthyl, dibenzo[a,d]cylcoheptenyl, and 1-, 2-, 3-, 4-, or 5-pyrenyl.

The aryl ring can optionally be substituted by one or more substituents. An "optionally substituted aryl" refers to an aryl having optionally one or more substituents (for example 1 to 5 substituents, for example 1, 2, 3 or 4) at any available point of attachment. Non-limiting examples of such substituents are selected from halogen, hydroxyl, oxo, nitro, amino, hydrazine, aminocarbonyl, azido, cyano, alkyl, cycloalkyl, alkenyl, alkynyl, cycloalkylalkyl, alkylamino, alkoxy, —$SO_2$—$NH_2$, aryl, heteroaryl, aralkyl, haloalkyl, haloalkoxy, alkoxycarbonyl, alkylaminocarbonyl, heteroarylalkyl, alkylsulfonamide, heterocyclyl, alkylcarbonylaminoalkyl, aryloxy, alkylcarbonyl, acyl, arylcarbonyl, aminocarbonyl, alkylsulfoxide, —$SO_2R^a$, alkylthio, carboxyl, and the like, wherein $R^a$ is alkyl or cycloalkyl.

Where a carbon atom in an aryl group is replaced with a heteroatom, the resultant ring is referred to herein as a heteroaryl ring.

The term "heteroaryl" as used herein by itself or as part of another group refers but is not limited to 5 to 12 carbon-atom aromatic rings or ring systems containing 1 to 3 rings which are fused together or linked covalently, typically containing 5 to 8 atoms; at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: methylenedioxyphenyl, pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, benzopyranyl, 1(4H)-benzopyranyl, 1(2H)-benzopyranyl, 3,4-dihydro-1(2H)-benzopyranyl, 3,4-dihydro-1 (2H)-benzopyranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1 (6H)-yl, 2-oxopyridin-1 (2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl, 7-azaindolyl, 6-azaindolyl, 5-azaindolyl, 4-azaindolyl. The term "pyrrolyl" (also called azolyl) as used herein includes pyrrol-1-yl, pyrrol-2-yl and pyrrol-3-yl. The term "furanyl" (also called "furyl") as used herein includes furan-2-yl and furan-3-yl (also called furan-2-yl and furan-3-yl). The term "thiophenyl" (also called "thienyl") as used herein includes thiophen-2-yl and thiophen-3-yl (also called thien-2-yl and thien-3-yl). The term "pyrazolyl" (also called 1H-pyrazolyl and 1,2-diazolyl) as used herein includes pyrazol-1-yl, pyrazol-3-yl, pyrazol-4-yl and pyrazol-5-yl. The term "imidazolyl" as used herein includes imidazol-1-yl, imidazol-2-yl, imidazol-4-yl and imidazol-5-yl. The term "oxazolyl" (also called 1,3-oxazolyl) as used herein includes oxazol-2-yl; oxazol-4-yl and oxazol-5-yl. The term "isoxazolyl" (also called 1,2-oxazolyl), as used herein includes isoxazol-3-yl, isoxazol-4-yl, and isoxazol-5-yl. The term "thiazolyl" (also called 1,3-thiazolyl), as used herein includes thiazol-2-yl, thiazol-4-yl and thiazol-5-yl (also called 2-thiazolyl, 4-thiazolyl and 5-thiazolyl). The term "isothiazolyl" (also called 1,2-thiazolyl) as used herein includes isothiazol-3-yl, isothiazol-4-yl, and isothiazol-5-yl. The term "triazolyl" as used herein includes 1H-triazolyl and 4H-1,2,4-triazolyl, "1H-triazolyl" includes 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl and 1H-1,2,4-triazol-5-yl. "4H-1,2,4-triazolyl" includes 4H-1,2,4-triazol-4-yl, and 4H-1,2,4-triazol-3-yl. The term "oxadiazolyl" as used herein includes 1,2,3-oxadiazol-4-yl, 1,2,3-oxadiazol-5-yl, 1,2,4-oxadiazol-3-yl, 1,2,4-oxadiazol-5-yl, 1,2,5-oxadiazol-3-yl and 1,3,4-oxadiazol-2-yl. The term "thiadiazolyl" as used herein includes 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl (also called furazan-3-yl) and 1,3,4-thiadiazol-2-yl. The term "tetrazolyl" as used herein includes 1H-tetrazol-1-yl, 1H-tetrazol-5-yl, 2H-tetrazol-2-yl, and 2H-tetrazol-5-yl. The term "oxatriazolyl" as used herein includes 1,2,3,4-oxatriazol-5-yl and 1,2,3,5-oxatriazol-4-yl. The term "thiatriazolyl" as used herein includes 1,2,3,4-thiatriazol-5-yl and 1,2,3,5-thiatriazol-4-yl. The term "pyridinyl" (also called "pyridyl") as used herein includes pyridin-2-yl, pyridin-3-yl and pyridin-4-yl (also called 2-pyridyl, 3-pyridyl and 4-pyridyl). The term "pyrimidyl" as used herein includes pyrimid-2-yl, pyrimid-4-yl, pyrimid-5-yl and pyrimid-6-yl. The term "pyrazinyl" as used herein includes pyrazin-2-yl and pyrazin-3-yl. The term "pyridazinyl as used herein includes pyridazin-3-yl and pyridazin-4-yl. The term "oxazinyl" (also called "1,4-oxazinyl") as used herein includes 1,4-oxazin-4-yl and 1,4-oxazin-5-yl. The term "dioxinyl" (also called "1,4-dioxinyl") as used herein includes 1,4-dioxin-2-yl and 1,4-dioxin-3-yl. The term "thiazinyl" (also called "1,4-thiazinyl") as used herein includes 1,4-thiazin-2-yl, 1,4-thiazin-3-yl, 1,4-thiazin-4-yl, 1,4-thiazin-5-yl and 1,4-thiazin-6-yl. The term "triazinyl" as used herein includes 1,3,5-triazin-2-yl, 1,2,4-triazin-3-yl, 1,2,4-triazin-5-yl, 1,2,4-triazin-6-yl, 1,2,3-triazin-4-yl and 1,2,3-triazin-5-yl. The term "imidazo[2,1-b][1,3]thiazolyl" as used herein includes imidazo[2,1-b][1,3]thiazol-2-yl, imidazo[2,1-b][1,3]thiazol-3-yl, imidazo[2,1-b][1,3]thiazol-5-yl and imidazo[2,1-b][1,3]thiazol-6-yl. The term "thieno[3,2-b]furanyl" as used herein includes thieno[3,2-b]furan-2-yl, thieno[3,2-b]furan-3-yl, thieno[3,2-b]furan-4-yl, and thieno[3,2-b]furan-5-yl. The term "thieno[3,2-b]thiophenyl" as used herein includes thieno[3,2-b]thien-2-yl, thieno[3,2-b]thien-3-yl, thieno[3,2-b]thien-5-yl and thieno[3,2-b]thien-6-yl. The term "thieno[2,3-d][1,3]thiazolyl" as used herein includes thieno[2,3-d][1,3]thiazol-2-yl, thieno[2,3-d][1,3]thiazol-5-yl and thieno[2,3-d][1,3]thiazol-6-yl. The term "thieno[2,3-d]imidazolyl" as used herein includes thieno[2,3-d]imidazol-2-yl, thieno[2,3-d]imidazol-4-yl and thieno[2,3-d]imidazol-5-yl. The term "tetrazolo[1,5-a]pyridinyl" as used herein includes tetrazolo[1,5-a]pyridine-5-yl, tetrazolo[1,5-a]pyridine-6-yl, tetrazolo[1,5-a]pyridine-7-yl, and tetrazolo[1,5-a]pyridine-8-yl. The term "indolyl" as used herein includes indol-1-yl, indol-2-yl, indol-3-yl, indol-4-yl, indol-5-yl, indol-6-yl and indol-7-yl. The term "indolizinyl" as used herein includes indolizin-1-yl, indolizin-2-yl, indolizin-3-yl, indolizin-5-yl, indolizin-6-yl, indolizin-7-yl, and indolizin-8-yl. The term "isoindolyl" as used herein includes isoindol-1-yl, isoindol-2-yl, isoindol-3-yl, isoindol-4-yl, isoindol-5-yl, isoindol-6-yl and isoindol-7-yl. The term "benzofuranyl" (also called benzo[b]furanyl) as used herein includes benzofuran-2-yl, benzofuran-3-yl, benzofuran-4-yl, benzofuran-5-yl, benzofuran-6-yl and benzofuran-7-yl. The term "isobenzofuranyl" (also called benzo[c]furanyl) as used herein includes isobenzofuran-1-yl, isobenzofuran-3-yl, isobenzofuran-4-yl, isobenzofuran-5-yl, isobenzofuran-6-yl and isobenzofuran-7-yl. The term "benzothiophenyl" (also called benzo[b]thienyl) as used herein includes 2-benzo[b]thiophenyl, 3-benzo[b]thiophenyl, 4-benzo[b]thiophenyl, 5-benzo[b]thiophenyl, 6-benzo[b]thiophenyl and -7-benzo[b]thiophenyl (also called benzothien-2-yl, benzothien-3-yl, benzothien-4-yl, benzothien-5-yl, benzothien-6-yl and benzothien-7-yl). The term "isobenzothiophenyl" (also called benzo[c]thienyl) as used herein includes isobenzothien-1-yl, isobenzothien-3-yl, isobenzothien-4-yl, isobenzothien-5-yl, isobenzothien-6-yl and isobenzothien-7-yl. The term "indazolyl" (also called 1H-indazolyl or 2-azaindolyl) as used herein includes 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, and 2H-indazol-7-yl. The term "benzimidazolyl" as used herein includes benzimidazol-1-yl, benzimidazol-2-yl, benzimidazol-4-yl, benzimidazol-5-yl, benzimidazol-6-yl and benzimidazol-7-yl. The term "1,3-benzoxazolyl" as used herein includes 1,3-benzoxazol-2-yl, 1,3-benzoxazol-4-yl, 1,3-benzoxazol-5-yl, 1,3-benzoxazol-6-yl and 1,3-benzoxazol-7-yl. The term "1,2-benzisoxazolyl" as used herein includes 1,2-benzisoxazol-3-yl, 1,2-benzisoxazol-4-yl, 1,2-benzisoxazol-5-yl, 1,2-benzisoxazol-6-yl and 1,2-benzisoxazol-7-yl. The term "2,1-benzisoxazolyl" as used herein includes 2,1-benzisoxazol-3-yl, 2,1-benzisoxazol-4-yl, 2,1-benzisoxazol-5-yl, 2,1-benzisoxazol-6-yl and 2,1-benzisoxazol-7-yl. The term "1,3-benzothiazolyl" as used herein includes 1,3-benzothiazol-2-yl, 1,3-benzothiazol-4-yl, 1,3-benzothiazol-5-yl, 1,3-benzothiazol-6-yl and 1,3-benzothiazol-7-yl. The term "1,2-benzoisothiazolyl" as used herein includes 1,2-benzisothiazol-3-yl, 1,2-benzisothiazol-4-yl, 1,2-benzisothiazol-5-yl, 1,2-benzisothiazol-6-yl and 1,2-benzisothiazol-7-yl. The term "2,1-benzoisothiazolyl" as used herein includes 2,1-benzisothiazol-3-yl, 2,1-benzisothiazol-4-yl, 2,1-benzisothiazol-5-yl, 2,1-benzisothiazol-6-yl and 2,1-benzisothiazol-7-yl. The term "benzotriazolyl" as used herein includes benzotriazol-1-yl, benzotriazol4-yl, benzotriazol-5-yl, benzotriazol-6-yl and benzotriazol-7-yl. The term "1,2,3-benzoxadiazolyl" as used herein includes 1,2,3-benzoxadiazol-4-yl, 1,2,3-benzoxadiazol-5-yl, 1,2,3-benzoxadiazol-6-yl and 1,2,3-benzoxadiazol-7-yl. The term "2,1,3-benzoxadiazolyl" as used herein includes 2,1,3-benzoxadiazol-4-yl, 2,1,3-benzoxadiazol-5-yl, 2,1,3-benzoxadiazol-6-yl and 2,1,3-benzoxadiazol-7-yl. The term "1,2,3-benzothiadiazolyl" as used herein includes 1,2,3-benzothiadiazol-4-yl, 1,2,3-benzothiadiazol-5-yl, 1,2,3-benzothiadiazol-6-yl and 1,2,3-benzothiadiazol-7-yl. The term "2,1,3-benzothiadiazolyl" as used herein includes 2,1,3-benzothiadiazol-4-yl, 2,1,3-benzothiadiazol-5-yl, 2,1,3-benzothiadiazol-6-yl and 2,1,3-benzothiadiazol-7-yl. The term "thienopyridinyl" as used herein includes thieno[2,3-b]pyridinyl, thieno[2,3-c]pyridinyl, thieno[3,2-c]pyridinyl and thieno[3,2-b]pyridinyl. The term "purinyl" as used herein includes purin-2-yl, purin-6-yl, purin-7-yl and purin-8-yl. The term "imidazo[1,2-a]pyridinyl", as used herein includes imidazo[1,2-a]pyridin-2-yl, imidazo[1,2-a]pyridin-3-yl, imidazo[1,2-a]pyridin-4-yl, imidazo[1,2-a] pyridin-5-yl, imidazo[1,2-a]pyridin-6-yl and imidazo[1,2-a]pyridin-7-yl. The term "1,3-benzodioxolyl", as used herein includes 1,3-benzodioxol-4-yl, 1,3-benzodioxol-5-yl, 1,3-benzodioxol-6-yl, and 1,3-benzodioxol-7-yl. The term "quinolinyl" as used herein includes quinolin-2-yl, quinolin-3-yl, quinolin-4-yl, quinolin-5-yl, quinolin-6-yl, quinolin-7-yl and quinolin-8-yl. The term "isoquinolinyl" as used herein includes isoquinolin-1-yl, isoquinolin-3-yl, isoquinolin-4-yl, isoquinolin-5-yl, isoquinolin-6-yl, isoquinolin-7-yl and isoquinolin-8-yl. The term "cinnolinyl" as used herein includes cinnolin-3-yl, cinnolin-4-yl, cinnolin-5-yl, cinnolin-6-yl, cinnolin-7-yl and cinnolin-8-yl. The term "quinazolinyl" as used herein includes quinazolin-2-yl, quiriazolin-4-yl, quinazolin-5-yl, quinazolin-6-yl, quinazolin-7-yl and quinazolin-8-yl. The term "quinoxalinyl". as used herein includes quinoxalin-2-yl, quinoxalin-5-yl, and quinoxalin-6-yl. The term "7-azaindolyl" as used herein refers to 1H-Pyrrolo[2,3-b]pyridinyl and includes 7-azaindol-1-yl, 7-azaindol-2-yl, 7-azaindol-3-yl, 7-azaindol-4-yl, 7-azaindol-5-yl, 7-azaindol-6-yl. The term "6-azaindolyl" as used herein refers to 1H-Pyrrolo[2,3-c]pyridinyl and includes 6-azaindol-1-yl, 6-azaindol-2-yl, 6-azaindol-3-yl, 6-azaindol-4-yl, 6-azaindol-5-yl, 6-azaindol-7-yl. The term "5-azaindolyl" as used herein refers to 1H-Pyrrolo[3,2-c]pyridinyl and includes 5-azaindol-1-yl, 5-azaindol-2-yl, 5-azaindol-3-yl, 5-azaindol-4-yl, 5-azaindol-6-yl, 5-azaindol-7-yl. The term "4-azaindolyl" as used herein refers to 1H-Pyrrolo[3,2-b]pyridinyl and includes 4-azaindol-1-yl, 4-azaindol-2-yl, 4-azaindol-3-yl, 4-azaindol-5-yl, 4-azaindol-6-yl, 4-azaindol-7-yl.

For example, non-limiting examples of heteroaryl can be 2- or 3-furyl, 2- or 3-thienyl, 1-, 2- or 3-pyrrolyl, 1-, 2-, 4- or 5-imidazolyl, 1-, 3-, 4- or 5-pyrazolyl, 3-, 4- or 5-isoxazolyl, 2-, 4- or 5-oxazolyl, 3-, 4- or 5-isothiazolyl, 2-, 4- or 5-thiazolyl, 1,2,3-triazol-1-, -4- or -5-yl, 1,2,4-triazol-1-, -3-, -4- or -5-yl, 1H-tetrazol-1-, or -5-yl, 2H-tetrazol-2-, or -5-yl, 1,2,3-oxadiazol-4- or -5-yl, 1,2,4-oxadiazol-3- or -5-yl, 1,2,5-oxadiazolyl, 1,3,4-oxadiazolyl, 1,2,3-thiadiazol-4- or -5-yl, 1,2,4-thiadiazol-3- or -5-yl, 1,2,5-thiadiazol-3- or -4-yl, 1,3,4-thiadiazolyl, 1- or 5-tetrazolyl, 2-, 3- or 4-pyridyl, 3- or 4-pyridazinyl, 2-, 4-, 5- or 6-pyrimidyl, 2-, 3-, 4-, 5- 6-2H-thiopyranyl, 2-, 3- or 4-4H-thiopyranyl, 4-azaindol-1-, 2-, 3-, 5-, or 7-yl, 5-azaindol-1-, or 2-, 3-, 4-, 6-, or 7-yl, 6-azaindol-1, 2-, 3-, 4-, 5-, or 7-yl, 7-azaindol-1-, 2-, 3-, 4, 5-, or 6-yl, 2-, 3-, 4-, 5-, 6- or 7-benzofuryl, 1-, 3-, 4- or 5-isobenzofuryl, 2-, 3-, 4-, 5-, 6- or 7-benzothienyl, 1-, 3-, 4- or 5-isobenzothienyl, 1-, 2-, 3-, 4-, 5-, 6- or 7-indolyl, 2- or 3-pyrazinyl, 1,4-oxazin-2- or -3-yl, 1,4-dioxin-2- or -3-yl, 1,4-thiazin-2- or -3-yl, 1,2,3-triazinyl, 1,2,4-triazinyl, 1,3,5-triazin-2-, -4- or -6-yl, thieno[2,3-b]furan-2-, -3-, -4-, or -5-yl, benzimidazol-1-yl, -2-yl, -4-yl, -5-yl, -6-yl, or -7-yl, 1-, 3-, 4-, 5-, 6- or 7-benzopyrazolyl, 3-, 4-, 5-, 6- or 7-benzisoxazolyl, 2-, 4-, 5-, 6- or 7-benzoxazolyl, 3-, 4-, 5-, 6- or 7-benzisothiazolyl, 1,3-benzothiazol-2-yl, -4-yl, -5-yl, -6-yl or -7-yl, 1,3-benzodioxol-4-yl, -5-yl, -6-yl, or -7-yl, benzotriazol-1-yl, -4-yl, -5-yl, -6-yl or -7-yl1-, 2-thianthrenyl, 3-, 4- or 5-isobenzofuranyl, 1-, 2-, 3-, 4- or 9-xanthenyl, 1-, 2-, 3- or 4-phenoxathiinyl, 2-, 3-pyrazinyl, 1-, 2-, 3-, 4-, 5-, 6-, 7- or 8-indolizinyl, 2-, 3-, 4- or 5-isoindolyl, 1H-indazol-1-yl, 3-yl, -4-yl, -5-yl, -6-yl, or -7-yl, 2H-indazol-2-yl, 3-yl, -4-yl, -5-yl, -6-yl, or -7-yl, imidazo[2,1-b][1,3]thiazoi-2-yl, imidazo[2,1-b][1,3]thiazol-3-yl, imidazo[2,1-b][1,3]thiazol-5-yl or imidazo[2,1-b][1,3]thiazol-6-yl, imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl or imidazo[1,2-a]pyridin-7-yl, tetrazolo[1,5-a]pyridine-5-yl, tetrazolo[1,5-a]pyridine-6-yl, tetrazolo[1,5-a]pyridine-7-yl, or tetrazolo[1,5-a]pyridine-8-yl, 2-, 6-, 7- or 8-purinyl, 4-, 5- or 6-phthalazinyl, 2-, 3- or 4-naphthyridinyl, 2-, 5- or 6-quinoxalinyl, 2-, 4-, 5-, 6-, 7- or 8-quinazolinyl, 1-, 2-, 3- or 4-quinolizinyl, 2-, 3-, 4-, 5-, 6-, 7-, or 8-quinolinyl(quinolyl), 2-, 4-, 5-, 6-, 7- or 8-quinazolyl, 1-, 3-, 4-, 5-, 6-, 7- or 8-isoquinolinyl(isoquinolyl), 3-, 4-, 5-, 6-, 7- or 8-cinnolinyl, 2-, 4-, 6- or 7-pteridinyl, 1-, 2-, 3-, 4- or 9-carbazolyl, 1-, 2-, 3-, 4-, 5-, 6-, 7-, 8- or 9-carbolinyl, 1-, 2-, 3-, 4-, 5-, 6-, 7-, 8-, 9- or 10-phenanthridinyl, 1-, 2-, 3- or 4-acridinyl, 1-, 2-, 3-, 4-, 5-, 6-, 7-, 8- or 9-perimidinyl, 2-, 3-, 4-, 5-, 6-, 7-, 8-, 9- or 10-(1,7)phenanthrolinyl, 1- or 2-phenazinyl, 1-, 2-, 3-, 4-, or 10-phenothiazinyl, 3- or 4-furazanyl, 1-, 2-, 3-, 4-, or 10-phenoxazinyl, or additionally substituted derivatives thereof.

An "optionally substituted heteroaryl" refers to a heteroaryl having optionally one or more substituents (for example 1 to 4 substituents, for example 1, 2, 3 or 4), selected from those defined above for substituted aryl.

The term "oxo" as used herein refers to the group =O.

The term "alkoxy" or "alkyloxy" as used herein refers to a radical having the Formula —$OR^b$ wherein $R^b$ is alkyl. Preferably, alkoxy is $C_1$-$C_{10}$ alkoxy, $C_1$-$C_6$ alkoxy, or $C_1$-$C_4$ alkoxy. Non-limiting examples of suitable alkoxy include methoxy, ethoxy, propoxy, isopropoxy, butoxy, isobutoxy, sec-butoxy, tert-butoxy, pentyloxy and hexyloxy. Where the oxygen atom in an alkoxy group is substituted with sulfur, the resultant radical is referred to as thioalkoxy. "Haloalkoxy" is an alkoxy group wherein one or more hydrogen atoms in the alkyl group are substituted with halogen. Non-limiting examples of suitable haloalkoxy include fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy, 2,2,2-trichloroethoxy; trichloromethoxy, 2-bromoethoxy, pentafluoroethyl, 3,3,3-trichloropropoxy, 4,4,4-trichlorobutoxy.

The term "aryloxy" as used herein denotes a group —O-aryl, wherein aryl is as defined above.

The term "arylcarbonyl" or "aroyl" as used herein denotes a group —C(O)-aryl, wherein aryl is as defined above.

The term "cycloalkylalkyl" by itself or as part of another substituent refers to a group having one of the aforementioned cycloalkyl groups attached to one of the aforementioned alkyl chains. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, 3-cyclopentylbutyl, cyclohexylbutyl and the like.

The term "heterocyclyl-alkyl" by itself or as part of another substituents refers to a group having one of the aforementioned heterocyclyl group attached to one of the aforementioned alkyl group, i.e., to a group —$R^d$—$R^c$ wherein $R^d$ is alkylene or alkylene substituted by alkyl group and $R^c$ is a heterocyclyl group.

The term "carboxy" or "carboxyl" or "hydroxycarbonyl" by itself or as part of another substituent refers to the group —$CO_2H$. Thus, a carboxyalkyl is an alkyl group as defined above having at least one substituent that is —$CO_2H$.

The term "alkoxycarbonyl" by itself or as part of another substituent refers to a carboxy group linked to an alkyl radical i.e. to form —C(=O)$OR^e$, wherein $R^e$ is as defined above for alkyl.

The term "alkylcarbonyloxy" by itself or as part of another substituent refers to a —O—C(=O)$R^e$ wherein $R^e$ is as defined above for alkyl.

The term "alkylcarbonylamino" by itself or as part of another substituent refers to an group of Formula —NH(C=O)R or —NR'(C=O)R, wherein R and R' are each independently alkyl or substituted alkyl.

The term "thiocarbonyl" by itself or as part of another substituent refers to the group —C(=S)—.

The term "alkoxy" by itself or as part of another substituent refers to a group consisting of an oxygen atom attached to one optionally substituted straight or branched alkyl group, cycloalkyl group, aralkyl, or cycloalkylalkyl group. Non-limiting examples of suitable alkoxy group include methoxy, ethoxy, n-propoxy, isopropoxy, n-butoxy, iso-butoxy, sec-butoxy, tert-butoxy, hexanoxy, and the like.

The term "halo" or "halogen" as a group or part of a group is generic for fluoro, chloro, bromo, or iodo.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl, and the like.

The term "haloaryl" alone or in combination, refers to an aryl radical having the meaning as defined above wherein one or more hydrogens are replaced with a halogen as defined above.

The term "haloalkoxy" alone or in combination refers to a group of Formula —O-alkyl wherein the alkyl group is substituted by 1, 2, or 3 halogen atoms. For example, "haloalkoxy" includes —$OCF_3$, —$OCHF_2$, —$OCH_2F$, —O—$CF_2$—$CF_3$, —O—$CH_2$—$CF_3$, —O—$CH_2$—$CHF_2$, and —O—$CH_2$—$CH_2F$.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

Where groups may be optionally substituted, such groups may be substituted once or more, and preferably once, twice or thrice. Substituents may be selected from, for example, the group comprising halogen, hydroxyl, oxo, nitro, amido, carboxy, amino, cyano haloalkoxy, and haloalkyl.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

As described herein, some of the compounds of the invention may contain one or more asymmetric carbon atoms that serve as a chiral center, which may lead to different optical forms (e.g. enantiomers or diastereoisomers). The invention comprises all such optical forms in all possible configurations, as well as mixtures thereof.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

Whenever used in the present invention the term "compounds of the invention" or a similar term is meant to include the compounds of general Formula I, Ia and Ib and any subgroup thereof. This term also refers to the compounds as depicted in Table 1, their derivatives, N-oxides, salts, solvates, hydrates, stereoisomeric forms, racemic mixtures, tautomeric forms, optical isomers, analogues, prodrugs, esters, and metabolites, as well as their quaternized nitrogen analogues. The N-oxide forms of said compounds are meant to comprise compounds wherein one or several nitrogen atoms are oxidized to the so-called N-oxide.

As used in the specification and the appended claims, the singular forms "a", "an", and "the" include plural referents unless the context clearly dictates otherwise. By way of example, "a compound" means one compound or more than one compound.

The terms described above and others used in the specification are well understood to those in the art.

In a particular embodiment, the present invention provides a compound of formula Ia;

wherein
$R_2$ is -halo;
$R_4$ and $R_5$ are each independently selected from —H, —$C_{1-8}$ alkyl, —$Ar_2$ and -$Het_1$; wherein said —$C_{1-8}$alkyl is optionally substituted with one or more substituents selected from —$Ar_2$;

$Ar_2$ is a 5- to 10-membered aromatic cycle; wherein said —$Ar_2$ is optionally substituted with one or more substituents selected from; -halo, —$C_{1-6}$alkyl, and —O—$C_{1-6}$alkyl; wherein said —$C_{1-6}$alkyl may be optionally substituted with from one to three -halo.

$Het_1$ is a 5- to 10-membered aromatic or non-aromatic heterocycle, optionally comprising 1 to 3 N, O or S atoms; wherein said $Het_1$ is optionally substituted with one or more substituents selected from -halo, —$C_{1-6}$ alkyl, —O—$C_{1-6}$ alkyl; wherein said —$C_{1-6}$ alkyl may be optionally substituted with from one to three -halo.

In yet a further specific embodiment, the present invention provides a compound according to the current invention in which the following restrictions apply:

$R_2$ is -halo; and $R_4$ and $R_5$ are each independently selected from —H, —$C_{1-8}$ alkyl and -phenyl.

Hence, the present invention provides a compound of formula Ia;

wherein $R_2$ is -halo;

$R_4$ and $R_5$ are each independently selected from —H, —$C_{1-8}$ alkyl, -phenyl.

Even more specifically, the present invention provides a compound of formula Ia;

Wherein $R_2$ is —Cl;

$R_4$ and $R_5$ are each independently selected from —H, —$C_{1-8}$ alkyl, -phenyl.

Alternatively, the present invention provides a compound of formula Ia;

Wherein $R_2$ is —F;

$R_4$ and $R_5$ are each independently selected from —H, —$C_{1-8}$ alkyl, -phenyl.

Alternatively, the present invention provides a compound of formula Ia;

Wherein $R_2$ is —Br;

$R_4$ and $R_5$ are each independently selected from —H, —$C_{1-8}$ alkyl, -phenyl.

In another embodiment, the present invention provides a compound of formula Ib;

wherein $R_2$ is -halo; and $R_3$ is selected from —H and —$C_{1-8}$ alkyl; and wherein said compound is not

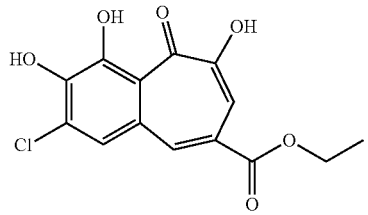 [SMILES: CCOC(=O)c1cc(O)c(=O)c2c(O)c(O)c(Cl)cc2c1]

In a specific embodiment, the present invention provides a compound of formula Ib
wherein
R$_2$ is —Cl; and
R$_3$ is selected from —H and —C$_{1-8}$ alkyl; and
wherein said compound is not

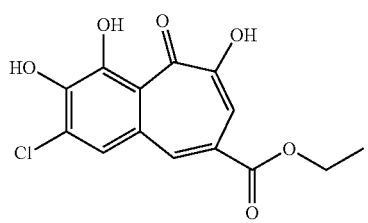 [SMILES: CCOC(=O)c1cc(O)c(=O)c2c(O)c(O)c(Cl)cc2c1]

Alternatively, the present invention provides a compound of formula Ib
wherein
R$_2$ is —F; and
R$_3$ is selected from —H and —C$_{1-8}$ alkyl.

Alternatively, the present invention provides a compound of formula Ib
wherein
R$_2$ is —Br; and
R$_3$ is selected from —H and —C$_{1-8}$ alkyl.

In yet a further embodiment, the present invention provides a compound according to the present invention in which the following restrictions apply:
R$_1$ is —(C=O)—O—R$_3$;
R$_2$ is -halo; and
R$_3$ is selected from —H and —C$_{3-8}$ alkyl.

In a specific embodiment, the present invention provides a compound of formula Ib
wherein
R$_2$ is —Cl; and
R$_3$ is selected from —H and —C$_{3-8}$ alkyl.

In another specific embodiment of the present invention, R$_2$ is selected from the list comprising —Cl, —F, and —Br.

In a more specific embodiment, the present invention provides a compound selected from the list comprising:

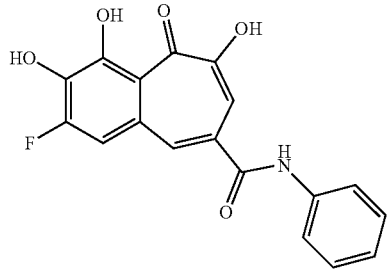

29

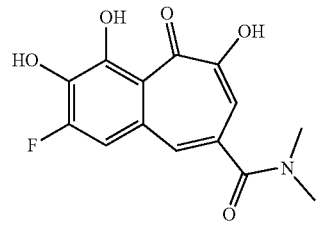

30

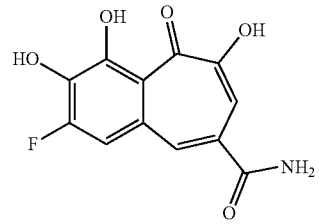

31

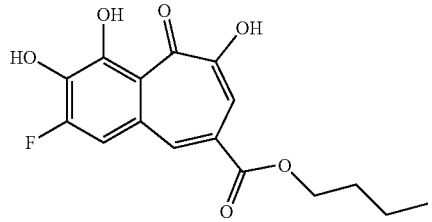

32

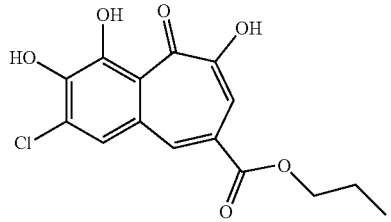

33

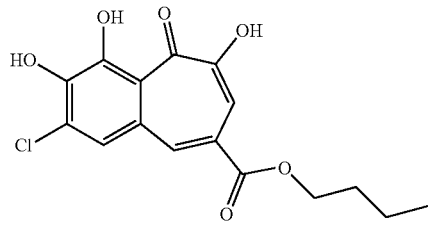

34

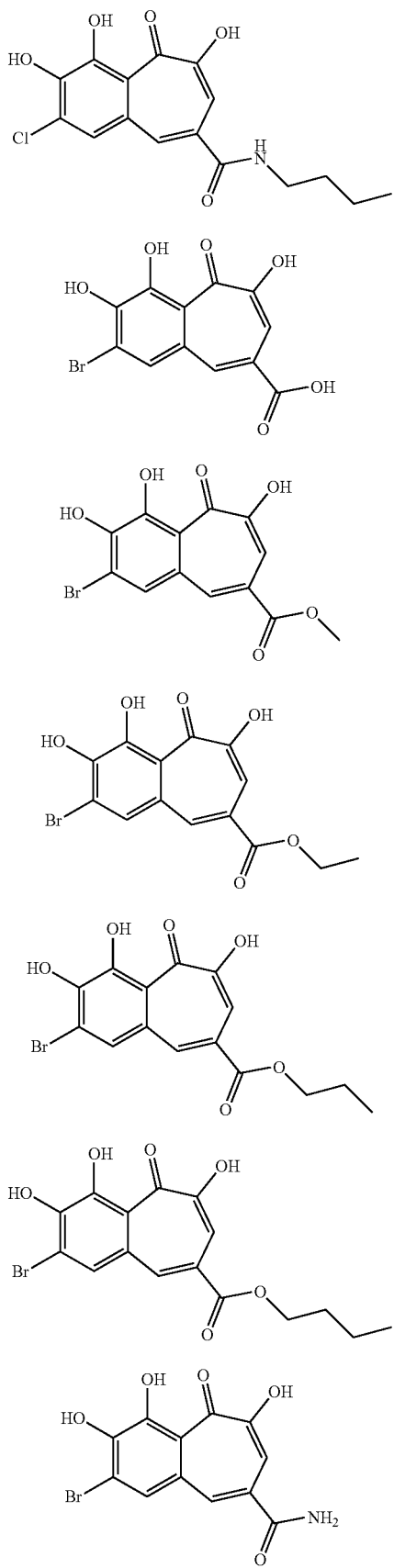
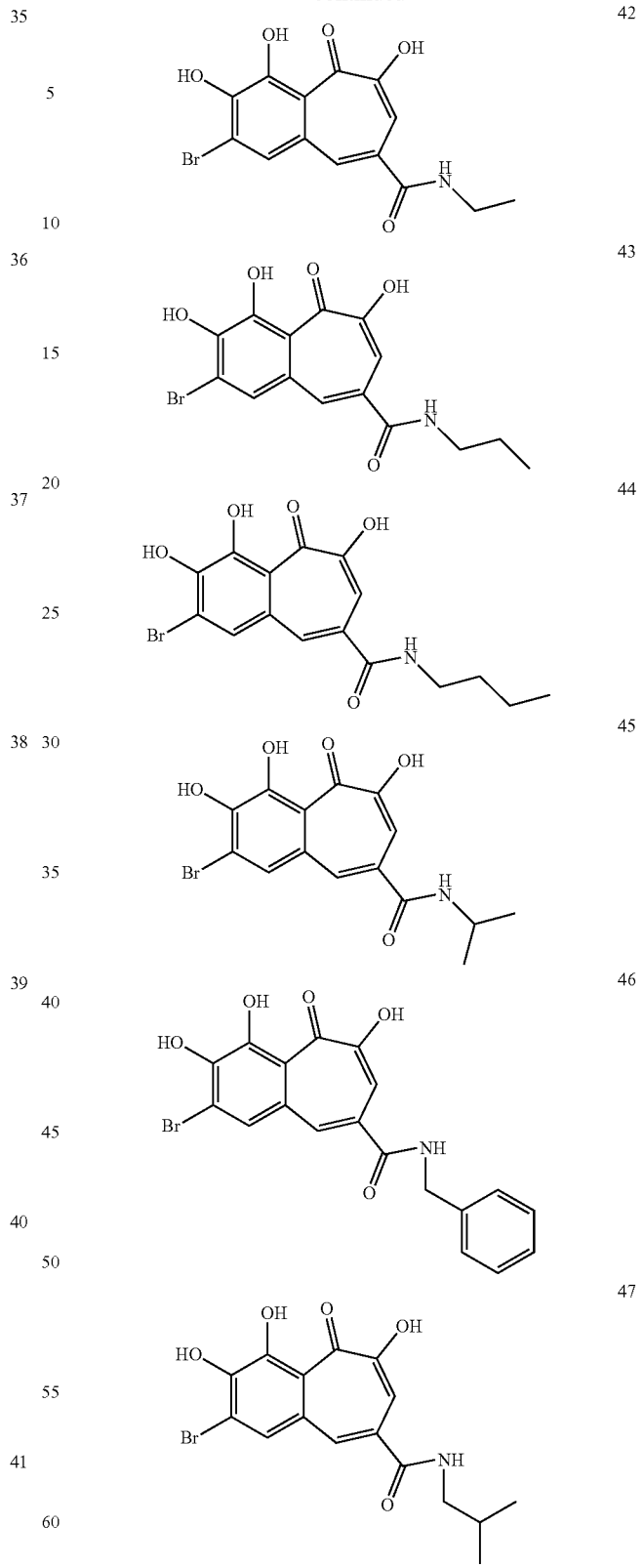
In a further aspect, the present invention provides a compound of Formula I or a stereoisomer, tautomer, racemic, metabolite, pro- or predrug, salt, hydrate, or solvate thereof,

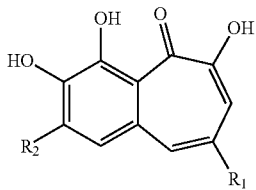

I wherein
R₁ is selected from —$C_{1-6}$ alkyl, —$Ar_1$, —(C=O)—O—$R_3$ and —(C=O)—$NR_4R_5$;
$R_2$ is -halo;
$R_3$ is selected from —H and —$C_{1-8}$ alkyl;
$R_4$ and $R_5$ are each independently selected from —H, —$C_{1-8}$ alkyl, —$Ar_2$ and -$Het_1$; wherein said —$C_{1-8}$alkyl is optionally substituted with one or more substituents selected from —$Ar_2$;
$Ar_1$ and $Ar_2$ are each independently a 5- to 10-membered aromatic cycle; wherein each of said —$Ar_1$ and —$Ar_2$ is optionally substituted with one or more substituents selected from; -halo, —$C_{1-6}$ alkyl, and —O—$C_{1-6}$ alkyl; wherein said —$C_{1-6}$ alkyl may be optionally substituted with from one to three -halo.
$Het_1$ is a 5- to 10-membered aromatic or non-aromatic heterocycle, optionally comprising 1 to 3 N, O or S atoms; wherein said $Het_1$ is optionally substituted with one or more substituents selected from -halo, —$C_{1-6}$ alkyl, —O—$C_{1-6}$ alkyl; wherein said —$C_{1-6}$ alkyl may be optionally substituted with from one to three -halo;
for use as a human or veterinary medicine; more in particular for use in the diagnosis, prevention and/or treatment of a cell proliferative disorder, such as cancer.

In a particular embodiment, the present invention provides a compound of formula Ia;

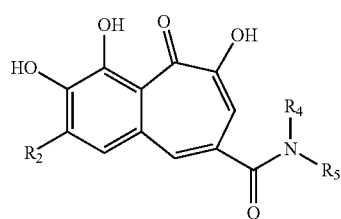

Ia wherein
$R_2$ is -halo;
$R_4$ and $R_5$ are each independently selected from —H, —$C_{1-8}$ alkyl, —$Ar_2$ and -$Het_1$; wherein said —$C_{1-8}$alkyl is optionally substituted with one or more substituents selected from —$Ar_2$;
$Ar_2$ is a 5- to 10-membered aromatic cycle; wherein said —$Ar_2$ is optionally substituted with one or more substituents selected from; -halo, —$C_{1-6}$alkyl, and —O—$C_{1-6}$alkyl; wherein said —$C_{1-6}$alkyl may be optionally substituted with from one to three -halo.
$Het_1$ is a 5- to 10-membered aromatic or non-aromatic heterocycle, optionally comprising 1 to 3 N, O or S atoms; wherein said $Het_1$ is optionally substituted with one or more substituents selected from -halo, —$C_{1-6}$ alkyl, —O—$C_{1-6}$ alkyl; wherein said —$C_{1-6}$ alkyl may be optionally substituted with from one to three -halo;
for use as a human or veterinary medicine; more in particular for use in the diagnosis, prevention and/or treatment of a cell proliferative disorder, such as cancer.

In yet a further specific embodiment, the present invention provides a compound according to the current invention in which the following restrictions apply:
$R_2$ is -halo; and
$R_4$ and $R_5$ are each independently selected from —H, —$C_{1-8}$ alkyl and -phenyl;
for use as a human or veterinary medicine.

Hence, the present invention provides a compound of formula Ia;
wherein
$R_2$ is -halo;
$R_4$ and $R_5$ are each independently selected from —H, —$C_{1-8}$ alkyl, -phenyl;
for use as a human or veterinary medicine; more in particular for use in the diagnosis, prevention and/or treatment of a cell proliferative disorder, such as cancer.

Even more specifically, the present invention provides a compound of formula Ia;
wherein
$R_2$ is —Cl;
$R_4$ and $R_5$ are each independently selected from —H, —$C_{1-8}$ alkyl, -phenyl;
for use as a human or veterinary medicine; more in particular for use in the diagnosis, prevention and/or treatment of a cell proliferative disorder, such as cancer.

Alternatively, the present invention provides a compound of formula Ia;
wherein
$R_2$ is —F;
$R_4$ and $R_5$ are each independently selected from —H, —$C_{1-8}$ alkyl, -phenyl;
for use as a human or veterinary medicine; more in particular for use in the diagnosis, prevention and/or treatment of a cell proliferative disorder, such as cancer.

Alternatively, the present invention provides a compound of formula Ia;
wherein
$R_2$ is —Br;
$R_4$ and $R_5$ are each independently selected from —H, —$C_{1-8}$ alkyl, -phenyl;
for use as a human or veterinary medicine; more in particular for use in the diagnosis, prevention and/or treatment of a cell proliferative disorder, such as cancer.

In another embodiment, the present invention provides a compound of formula Ib;

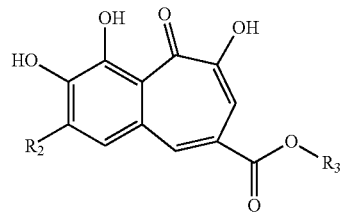

Ib wherein
$R_2$ is -halo; and
$R_3$ is selected from —H and —$C_{1-8}$ alkyl;
for use as a human or veterinary medicine; more in particular for use in the diagnosis, prevention and/or treatment of a cell proliferative disorder, such as cancer.

In a specific embodiment, the present invention provides a compound of formula Ib
wherein
  R$_2$ is —Cl; and
  R$_3$ is selected from —H and —C$_{1-8}$ alkyl;
for use as a human or veterinary medicine; more in particular for use in the diagnosis, prevention and/or treatment of a cell proliferative disorder, such as cancer.

Alternatively, the present invention provides a compound of formula Ib
wherein
  R$_2$ is —F; and
  R$_3$ is selected from —H and —C$_{1-8}$ alkyl;
for use as a human or veterinary medicine; more in particular for use in the diagnosis, prevention and/or treatment of a cell proliferative disorder, such as cancer.

Alternatively, the present invention provides a compound of formula Ib
wherein
  R$_2$ is —Br; and
  R$_3$ is selected from —H and —C$_{1-8}$ alkyl;
for use as a human or veterinary medicine; more in particular for use in the diagnosis, prevention and/or treatment of a cell proliferative disorder, such as cancer.

In yet a further embodiment, the present invention provides a compound according to the present invention in which the following restrictions apply:
  R$_1$ is —(C═O)—O—R$_3$;
  R$_2$ is -halo; and
  R$_3$ is selected from —H and —C$_{3-8}$ alkyl;
for use as a human or veterinary medicine; more in particular for use in the diagnosis, prevention and/or treatment of a cell proliferative disorder, such as cancer.

In a specific embodiment, the present invention provides a compound of formula Ib
wherein
  R$_2$ is —Cl; and
  R$_3$ is selected from —H and —C$_{3-8}$ alkyl;
for use as a human or veterinary medicine; more in particular for use in the diagnosis, prevention and/or treatment of a cell proliferative disorder, such as cancer.

In a more specific embodiment, the present invention provides a compound for use as a human or veterinary medicine; more in particular for use in the diagnosis, prevention and/or treatment of a cell proliferative disorder, such as cancer wherein said compound is selected from the list comprising:

29
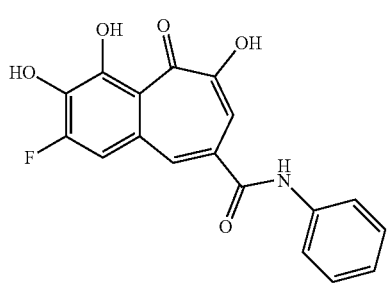

30
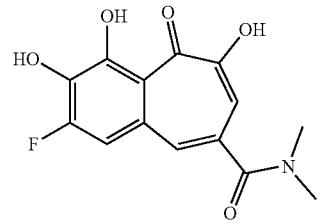

31
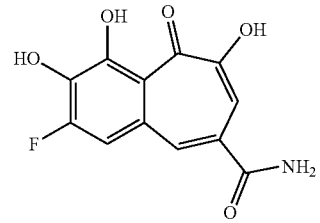

32
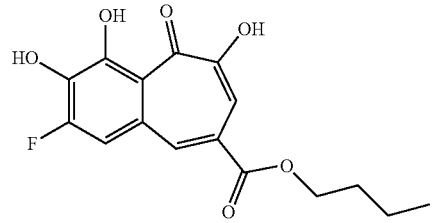

33
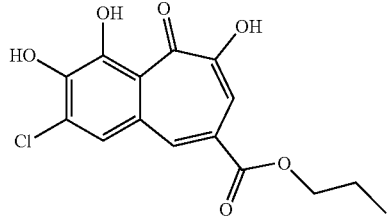

34
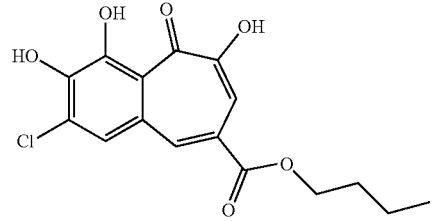

35
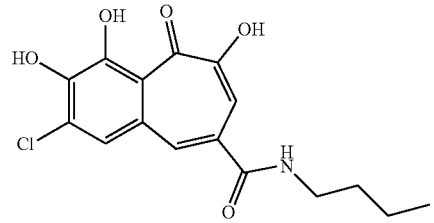

36
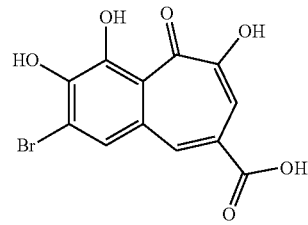

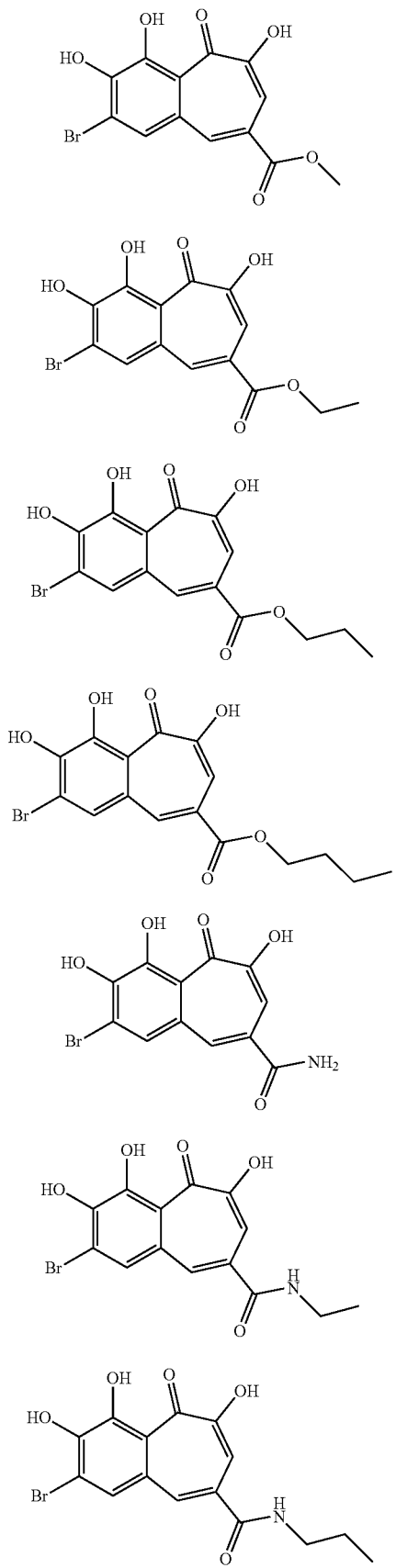

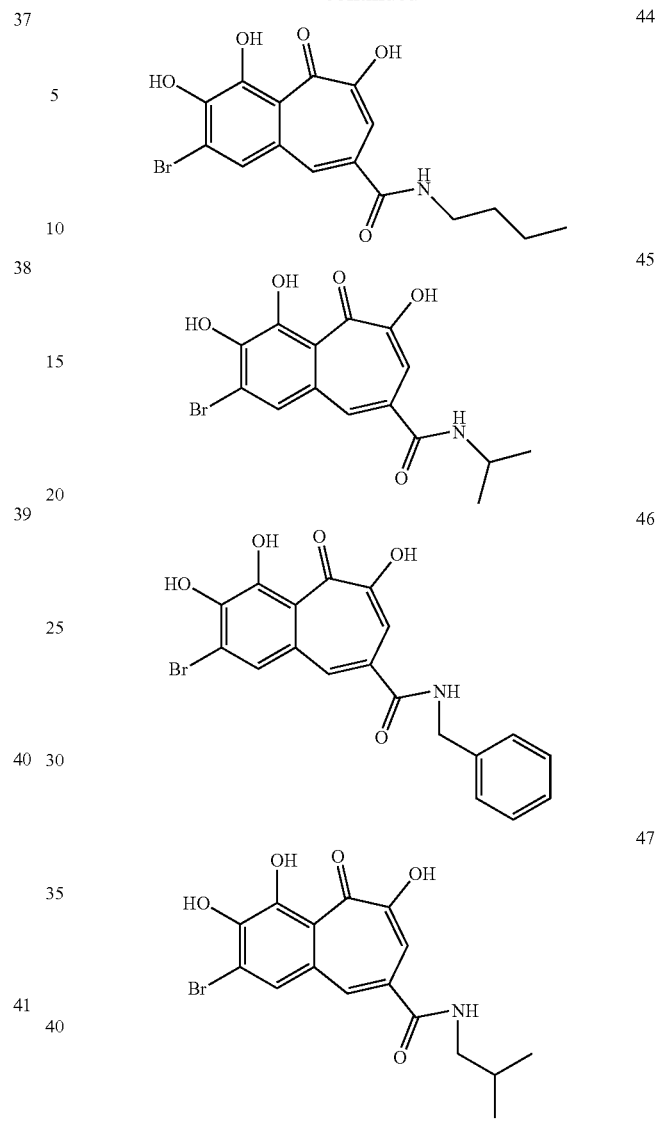

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

In a preferred embodiment, the compounds of the present invention are useful as Atg4B inhibitors. Hence, in a further aspect, the present invention provides the use of a compound as defined herein for inhibiting Atg4B activity either in vivo or in vitro.

The present invention further provides the use of a compound as defined hereinbefore or the use of a composition comprising said compound, as a human or veterinary medicine, in particular for the diagnosis, prevention and/or treatment of a cell proliferative disorder, such as cancer.

The present invention further provides a compound as defined hereinbefore or a composition comprising said compound for use in the diagnosis, prevention and/or treatment of a cell proliferative disorder, such as cancer.

In a preferred embodiment, the invention provides a compound as defined hereinbefore or a composition comprising said compound for use in the diagnosis, prevention and/or treatment of a cell proliferative disorder, such as cancer.

Method of Treatment

The present invention further provides a method for the prevention and/or treatment of a cell proliferative disorder, such as cancer; said method comprising administering to a subject in need thereof a therapeutically effective amount of a compound as defined herein, or a pharmaceutical composition as defined herein.

As already indicated herein above, the compounds of the present invention are Atg4B inhibitors, said inhibition may be effected in vitro and/or in vivo, and when effected in vivo, is preferably effected in a selective manner.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. Nos. 6,372,778, 6,369,086, 6,369,087 and 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

Generally, for pharmaceutical use, the compounds of the inventions may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is again made to for instance U.S. Pat. Nos. 6,372,778, 6,369,086, 6,369,087 and 6,372,733, as well as to the standard handbooks, such as the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, creams, lotions, soft and hard gelatin capsules, suppositories, eye drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein, for example using liposomes or hydrophilic polymeric matrices based on natural gels or synthetic polymers. In order to enhance the solubility and/or the stability of the compounds of a pharmaceutical composition according to the invention, it can be advantageous to employ α-, β- or γ-cyclodextrins or their derivatives. An interesting way of formulating the compounds in combination with a cyclodextrin or a derivative thereof has been described in EP-A-721,331. In particular, the present invention encompasses a pharmaceutical composition comprising an effective amount of a compound according to the invention with a pharmaceutically acceptable cyclodextrin.

In addition, co-solvents such as alcohols may improve the solubility and/or the stability of the compounds. In the preparation of aqueous compositions, addition of salts of the compounds of the invention can be more suitable due to their increased water solubility.

Particular reference is made to the compositions, formulations (and carriers, excipients, diluents, etc. for use therein), routes of administration etc., which are known per se for analogous pyridinocarboxamides, such as those described in U.S. Pat. No. 4,997,834 and EP-A-0 370 498.

More in particular, the compositions may be formulated in a pharmaceutical formulation comprising a therapeutically effective amount of particles consisting of a solid dispersion of the compounds of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

It may further be convenient to formulate the compounds in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The preparations may be prepared in a manner known per se, which usually involves mixing at least one compound according to the invention with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holderor container (which may be properly labeled); optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds can be administered by a variety of routes including the oral, rectal, ocular, transdermal, subcutaneous, intravenous, intramuscular or intranasal routes, depending mainly on the specific preparation used and the condition to be treated or prevented, and with oral and intravenous administration usually being preferred. The at least one compound of the invention will generally be administered in an "effective amount", by which is meant any amount of a compound of the Formula I, II or III or any subgroup thereof that, upon suitable administration, is sufficient to achieve the desired therapeutic or prophylactic effect in the individual to which it is administered. Usually, depending on the condition to be prevented or treated and the route of administration, such an effective amount will usually be between 0.01 to 1000 mg per kilogram body weight day of the patient per day, more often between 0.1 and 500 mg, such as between 1 and 250 mg, for example about 5, 10, 20, 50, 100, 150, 200 or 250 mg, per kilogram body weight day of the patient per day, which may be administered as a single daily dose, divided over one or more daily doses, or essentially continuously, e.g. using a drip infusion. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous administration, the compound according to the invention, if desired with the substances customary therefore such as solubilizers, emulsifiers or further auxiliaries are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquefy and/or dissolve in the rectal cavity to release the drug.

In preferred embodiments, the compounds and compositions of the invention are used locally, for instance topical or in both absorbed and non-adsorbed applications.

The compositions are of value in the veterinary field, which for the purposes herein not only includes the prevention and/or treatment of diseases in animals, but also—for economically important animals such as cattle, pigs, sheep, chicken, fish, etc.—enhancing the growth and/or weight of the animal and/or the amount and/or the quality of the meat or other products obtained from the animal. Thus, in a further aspect, the invention relates to a composition for veterinary use that contains at least one compound of the invention and at least one suitable carrier (i.e. a carrier suitable for veterinary use). The invention also relates to the use of a compound of the invention in the preparation of such a composition.

The invention will now be illustrated by means of the following synthetic and biological examples, which do not limit the scope of the invention in any way.

EXAMPLES

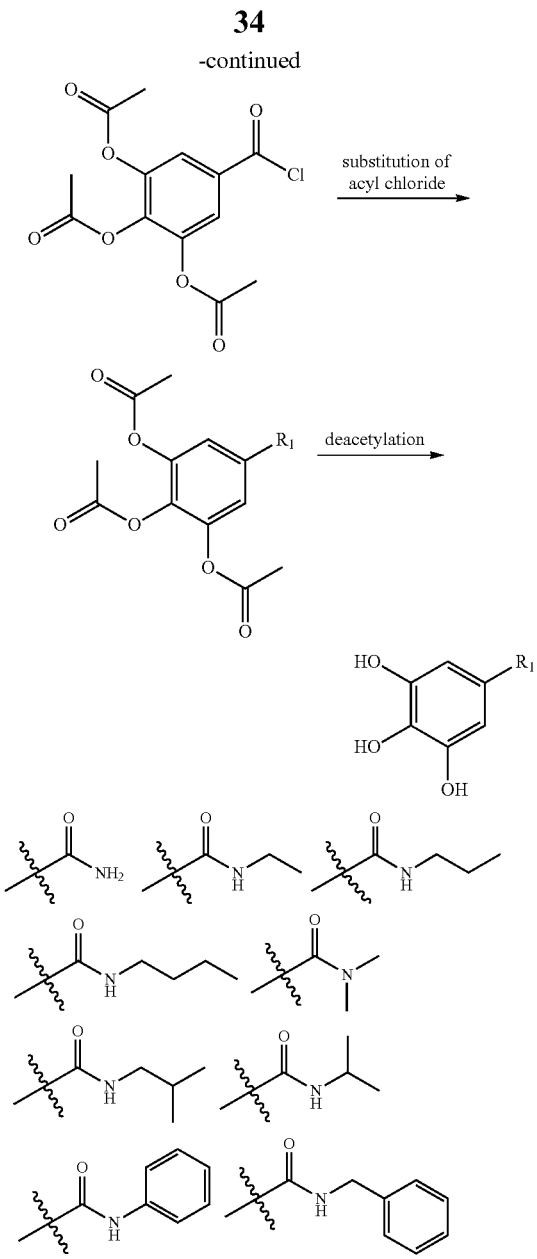

Scheme 1: General synthetic scheme for the synthesis of gallamides

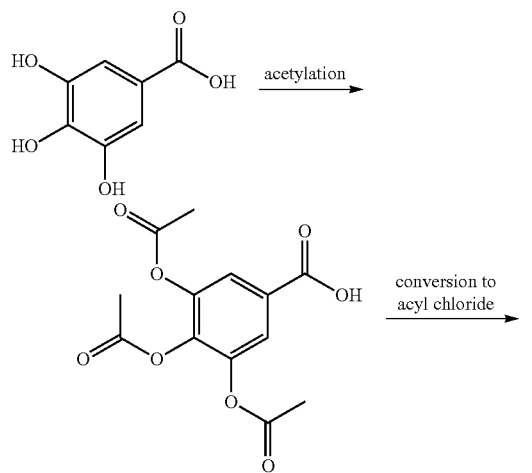

Scheme 2: General synthetic scheme for the synthesis of gallic acid ester derivatives

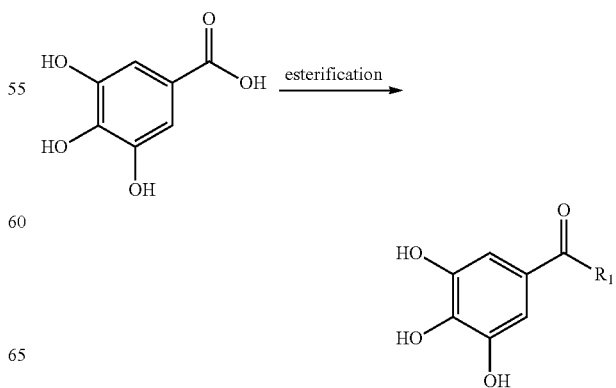

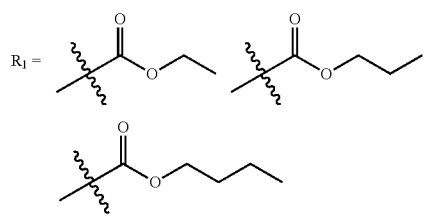

Scheme 3: General synthetic scheme for the oxidative benzotropolone synthesis

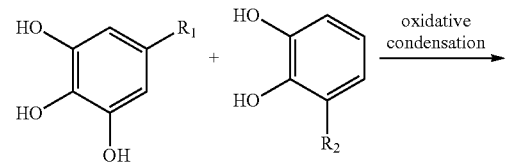

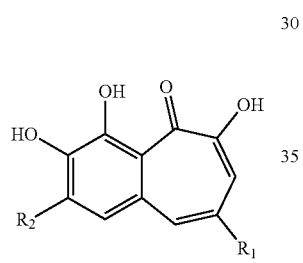

$R_2$ = F, Cl, Br

Scheme 4: Synthesis of gallamides.

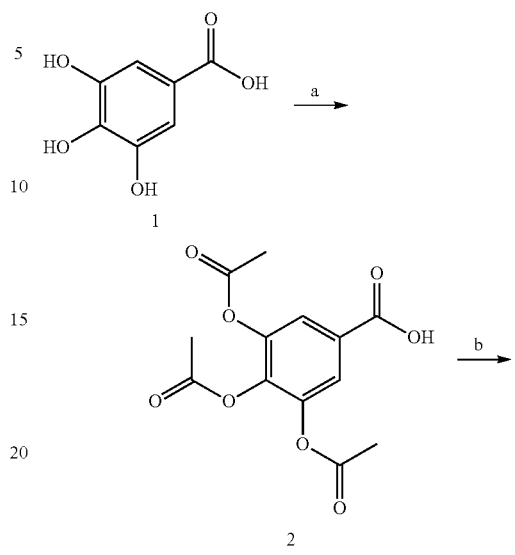

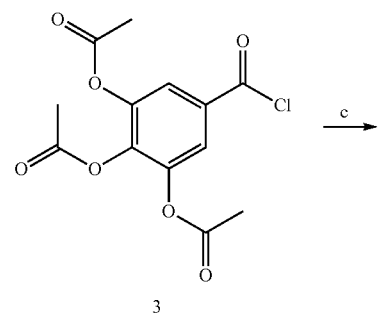

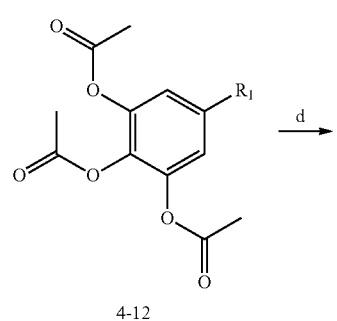

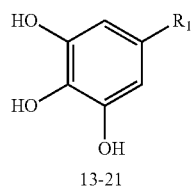

Scheme 4 shows the synthesis of gallamides. Variations at the $R_1$-position were incorporated by derivatisation of the carboxylic acid of the commercially available 3,4,5-trihydroxybenzoic acid (1), with formation of gallamides 13-21 as a result. Synthesis was initiated by acetylation of (1) using acetic anhydride and a catalytic amount of $H_2SO_4$ to yield the 3,4,5-triacetoxybenzoic acid (2). The free carboxylic acid was then converted to the acyl chloride using thionyl chloride with formation of 5-(chlorocarbonyl)benzene-1,2,3-triyl triacetate (3). Next, the amine of interest was added and compounds 4-12 were obtained. Deacetylation with hydrazine afforded the corresponding gallamides 13-21.

Gallic acid ester derivatives were obtained by addition of the alcohol of interest to 3,4,5-trihydroxybenzoic acid (1). The reaction was allowed to reflux overnight to yield gallic acid ester derivatives 22-24 and is shown in Scheme 5.

Oxidative condensation of gallamides 13-21 or gallic acid ester derivatives 22-24 or the commercially available methyl 3,4,5-trihydroxybenzoate 25 with commercially available catechols 26-28 afforded benzotropolones 29-47 as shown in Scheme 6.

-continued

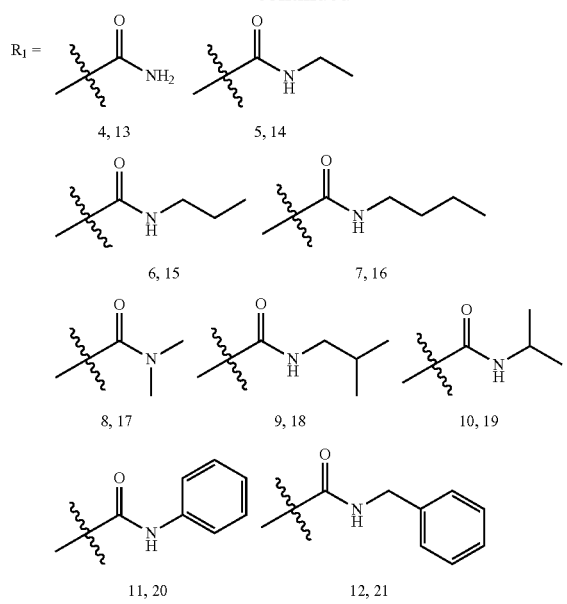

Reagents and conditions: (a) Ac₂O, H₂SO₄ (cat.), 80° C., 15'; (b) Dry toluene, SOCl₂, reflux, 1.5 h; (c) Amine of interest, dry DCM, DIPEA, rt, 1 h; (d) ACN, NH₂NH₂•H₂O, rt, 0.5 h.

Scheme 5: Synthesis of gallic acid ester derivatives.

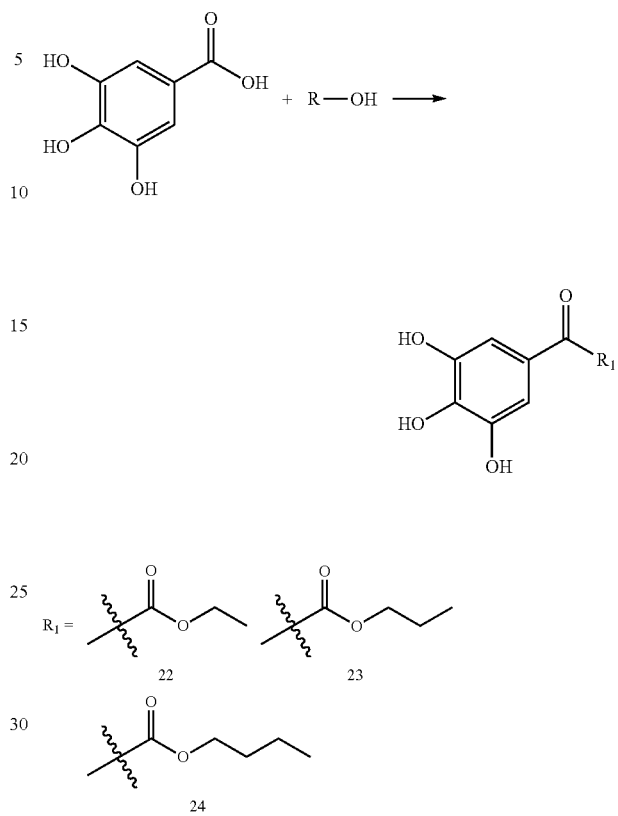

Reagents and conditions: Alcohol of interest, H₂SO₄ (cat.), reflux, overnight.

Scheme 6: Benzotropolone synthesis.

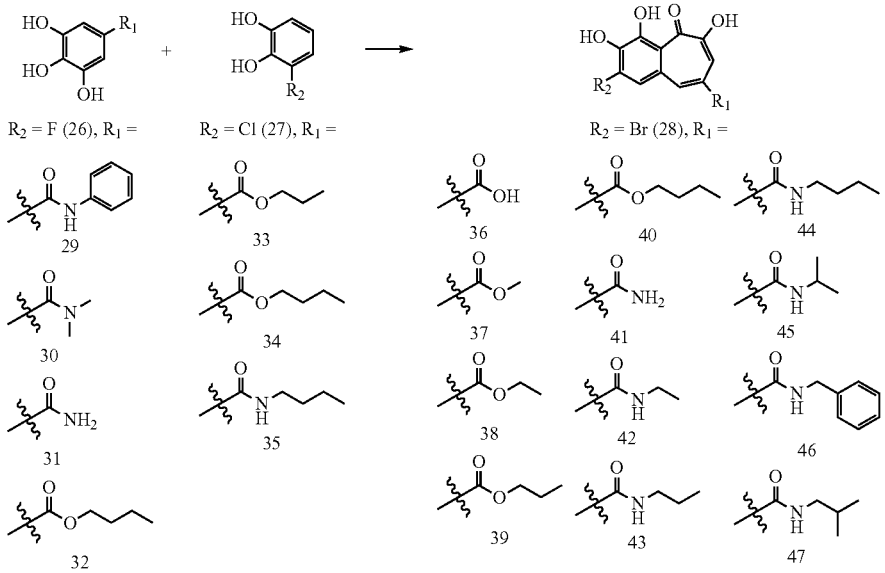

Reagents and conditions: Gallic acid derivative, pyrocatechol derivative, Acetone/H₂O 1:4; KIO₃ in H₂O added dropwise, rt, 1.5 h.

EXPERIMENTAL PROCEDURES

Chemistry

Reagents were purchased from Sigma-Aldrich, Acros, Fluorochem or TCI Chemicals and were used without further purification. Synthesized compounds were characterized with 1H-NMR and mass spectrometry. NMR spectra were recorded on a 400 MHz Bruker Avance DRX-400 spectrometer and analyzed by MestReNova analytical software. Chemical shifts are expressed in ppm and coupling constants are in Hertz (Hz). ES mass spectra were obtained from an Esquire 3000plus iontrap mass spectrometer from Bruker Daltonics. Purity was determined using two diverse HPLC systems based on either mass detection or UV detection. A Waters acquity UPLC system coupled to a Waters TUV detector and Waters TQD ESI mass spectrometer was applied. A waters acquity UPLC BEH C18 1.7 μm 2.1×50 mm column was used. Solvent A: water with 0.1% formic acid, solvent B: acetonitrile with 0.1% formic acid. Method I: 0.15 min 95% A, 5% B then in 1.85 min from 95% A, 5% B to 95% B, 5% A, then 0.25 min (0.350 mL/min), 95% B, 5% A. The wavelength for UV detection was 254 nm. Method 11: flow 0.4 mL/min, 0.25 min 95% A, 5% B, then in 4.75 min to 95% B, 5% A, then 0.25 min 95% B, 5% A, followed by 0.75 min 95% A, 5% B. The wavelength for UV detection was 214 nm. Where necessary flash purification was performed on a Biotage Isolera One flash system equipped with internal variable dual-wavelength diode array detector (200-400 nm). SNAP cartridges used for normal phase and reversed phase flash purification were respectively KP-Sil (10 g, 25 g, 50 g, flow rate of 10-50 mL/min) and KP-C18-HS (12 g, 30 g, flow rate of 10-30 mL/min). Eluting gradients used varied by purification. Dry sample loading was done by self-packing samplet cartridges using silica or Celite 545, respectively, for normal and reversed phase purifications. A Waters preparatory HPLC system was used for difficult purifications. The typical solvents were (A) 0.1% formic acid in water and (B) 0.1% formic acid in methanol. The column was a Waters Xbridge C18, 19×100 mm with 5 μm particle size. The typical flow was 17 mL/min and a typical gradient took 13 to 22 min using a gradient of solvents A and B. Separations by preparative TLC were performed using Analtech Uniplate thin layer chromatography plates with a 20×20 cm 2000 microns silica gel layer. Lyophilisation was performed by a Christ Alpha 1-2 LDplus Freeze Dryer using a 1:1 ratio of water/tert-butanol.

Synthetic Procedure A

Intermediate 2: 3,4,5-triacetoxybenzoic Acid

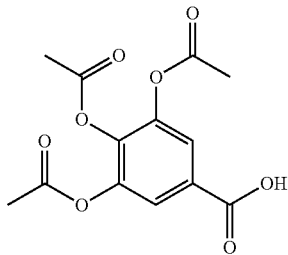 [SMILES: CC(=O)Oc1cc(C(=O)O)cc(OC(C)=O)c1OC(C)=O]

One equivalent of 3,4,5-trihydroxybenzoic acid (1) (6 g, 35.3 mmol) was suspended in 7.5 equivalents of acetic anhydride. The obtained suspension was stirred and 10 drops of sulphuric acid were added catalytically. The solution was heated at 80° C. for 15 minutes, then left to cool to room temperature. 150 mL of ice water was added to the solution, initiating the formation of a white precipitate. The mixture was left standing for 2 hours, allowing formation of white crystals. The precipitate was filtered off and dried under high vacuum to yield 3,4,5-triacetoxybenzoic acid (8.38 g, 28.26 mmol) as white crystals. (Yield: 80%)

$^1$H NMR (400 MHz, DMSO-d6) δ 2.30 (s, 6H), 2.33 (s, 3H), 7.75 (s, 2H), 13.40 (s, 1H).

$t_R$ 1.45 min, MS (ESI) m/z 294.1 [M−H] (100%)

Synthetic Procedure B

Intermediate 3: 5-(chlorocarbonyl)benzene-1,2,3-triyl Triacetate

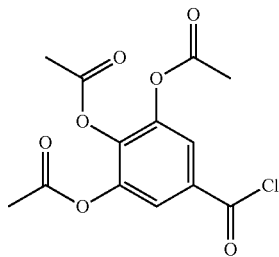 [SMILES: CC(=O)Oc1cc(C(=O)Cl)cc(OC(C)=O)c1OC(C)=O]

3,4,5-triacetoxybenzoic acid (2) (8.38 g, 28.26 mmol) was suspended in 30 mL of dry toluene. Afterwards, 3 equivalents of thionyl chloride were added dropwise. The mixture was refluxed for 90 minutes, then allowed to cool to room temperature. Volatiles were evaporated using a rotary evaporator, with formation of a white precipitate to give 5-(chlorocarbonyl)benzene-1,2,3-triyl triacetate (7.83 g, 24.89 mmol) as a white precipitate. (Yield: 88%)

Synthetic Procedure C

To a stirred solution of the amine of interest (1.5 eq.) in 20 mL of dry DCM was added 1 eq. of 5-(chlorocarbonyl)benzene-1,2,3-triyl triacetate (3) followed by addition of 1.5 eq. of N-ethyl-N-isopropylpropan-2-amine. The solution was stirred for 1 h at room temperature and was afterwards evaporated to dryness to give an oily mixture. The reaction mixture was extracted using 3×20 mL DCM and subsequently 20 mL 1M HCl, 20 mL saturated NaCl and Na$_2$SO$_4$. The organic layers were pooled and evaporated to dryness to yield the desired intermediate 4-12 as a yellow oil. Intermediates 4-12 were found pure using UPLC and were used as starting compounds in synthetic procedure D without further analysis.

Synthetic Procedure D

Intermediate 4-12 was dissolved in 20 mL of acetonitrile while stirring at room temperature. Afterwards, 6 eq. of hydrazine monohydrate were added to the reaction mixture. After allowing the mixture to stir for 30 minutes at room temperature, 2 M HCl was added until a pH value of 3 was obtained. The mixture was extracted with 3×20 mL of ethyl acetate, and the combined organic layers were washed with 10 mL of saturated NaCl solution, followed by drying over MgSO₄. Volatiles were evaporated using a rotary evaporator to give the desired deacetylated gallamide 13-21.

Intermediate 13: 3,4,5-trihydroxybenzamide

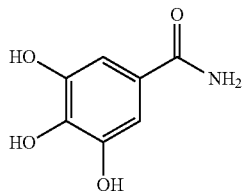 [SMILES: NC(=O)c1cc(O)c(O)c(O)c1]

Following synthetic procedure D, ammonia (61.0 mL, 30.5 mmol) was used to afford the intermediate 5-carbamoylbenzene-1,2,3-triyl triacetate (4) (5.6 g, 18.97 mmol, yield: 93%), which was deacetylated to obtain the desired 3,4,5-trihydroxybenzamide (0.500 g, 2.96 mmol) as a pure solid. (Yield: 16%)
¹H NMR (400 MHz, DMSO-d₆) δ 6.55 (s, 2H), 8.44 (s, 2H), 8.71 (s, 1H), 9.40 (s, 2H).
$t_R$ 0.25 min, MS (ESI) m/z 168.1 [M−H] (100%)

Intermediate 14: N-ethyl-3,4,5-trihydroxybenzamide

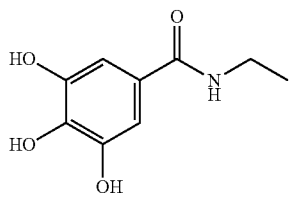

Following synthetic procedure D, ethylamine (2M in THF, 2.86 mL, 5.72 mmol) was used to afford the intermediate 5-(ethylcarbamoyl)benzene-1,2,3-triyl triacetate (5) (1.233 g, 3.81 mmol, yield: 100%), which was deacetylated to obtain the desired N-ethyl-3,4,5-trihydroxybenzamide (0.420 g, 2.13 mmol) as a yellow oil. (Yield: 55.8%)
¹H NMR (400 MHz, DMSO-d₆) δ 1.06 (t, J=7.2 Hz, 3H), 3.09-3.24 (m, 2H), 6.80 (s, 2H), 7.87 (s, 1H), 8.06 (t, J=5.1 Hz, 1H).
$t_R$ 0.26 min, MS (ESI) m/z 198.1 [M+H] (96%)

Intermediate 15: N-propyl-3,4,5-trihydroxybenzamide

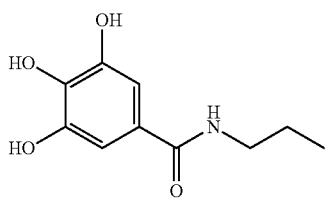

Following synthetic procedure D, n-propyl amine (0.470 mL, 5.72 mmol) was used to afford the intermediate 5-(propylcarbamoyl)benzene-1,2,3-triyl triacetate (6) (1.286 g, 3.81 mmol, yield: 100%), which was deacetylated to obtain the desired 5-(propylcarbamoyl)benzene-1,2,3-triyl triacetate (0.491 g, 2.32 mmol) as a colourless oil. (Yield: 61%)
¹H NMR (400 MHz, DMSO-d₆) δ 0.83 (m, 2H), 1.41-1.53 (m, 2H), 3.08-3.19 (m, 2H), 6.82 (s, 2H), 7.82 (s, 1H), 8.06 (s, 1H), 9.01 (s, 2H).
$t_R$ 0.75 min, MS (ESI) m/z 212.1 [M+H] (95%)

Intermediate 16: N-butyl-3,4,5-trihydroxybenzamide

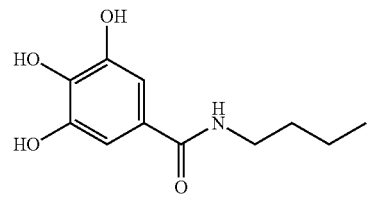 [SMILES: CCCCNC(=O)c1cc(O)c(O)c(O)c1]

Following synthetic procedure D, butan-1-amine (0.507 g, 6.93 mmol) was used to afford the intermediate 5-(butylcarbamoyl)benzene-1,2,3-triyl triacetate (7) (1.73 g, 4.92 mmol, yield: 107%), which was deacetylated to obtain the desired N-butyl-3,4,5-trihydroxybenzamide (1.23 g, 5.46 mmol). (Yield: 111%)
¹H NMR (400 MHz, DMSO-d₆) δ 0.87 (m, 3H), 1.22-1.32 (m, 4H), 3.16 (q, J=6.9 Hz, J'=12.8 Hz, 2H), 6.80 (s, 2H), 7.80 (s, 1H), 8.03 (t, J=5.6 Hz, 1H), 9.00 (s, 2H).
$t_R$ 1.39 min, MS (ESI) m/z 227.3 [M+H] (100%)

Intermediate 17: 3,4,5-trihydroxy-N,N-dimethylbenzamide

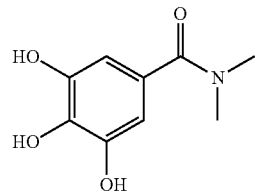

Following synthetic procedure D, dimethylamine (14.30 g, 28.6 mmol) was used to afford the intermediate 5-(dimethylcarbamoyl)benzene-1,2,3-triyl triacetate (8) (5.1 g, 15.77 mmol, yield: 83%), which was deacetylated to obtain the desired 3,4,5-trihydroxy-N,N-dimethylbenzamide (4.27 g, 21.65 mmol), as a brown solid. (Yield: 137%)
¹H NMR (400 MHz, DMSO-d₆) δ 2.90 (s, 6H), 6.33 (s, 2H), 8.86 (s, 1H), 9.20 (s, 2H).
$t_R$ 0.27 min, MS (ESI) m/z 198.1 [M−H] (95%)

Intermediate 18: 3,4,5-trihydroxy-N-isobutylbenzamide

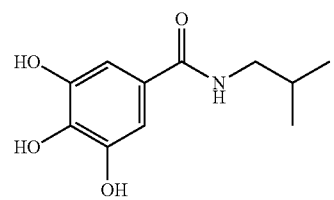 [SMILES: CC(C)CNC(=O)c1cc(O)c(O)c(O)c1]

Following synthetic procedure D, isobutylamine (0.293 g, 4.01 mmol) was used to afford the intermediate 5-(isobutylcarbamoyl)benzene-1,2,3-triyl triacetate (9) (0.638 g, 1.816 mmol, yield: 68%), which was deacetylated to obtain the desired 3,4,5-trihydroxy-N-isobutylbenzamide (0.278 g, 1.23 mmol) as a pure solid. (Yield: 68%)

$^1$H NMR (400 MHz, DMSO-$d_6$) δ 0.85 (d, J=6.7 Hz, 6H), 1.79 (m, 1H), 2.99 (t, J=6.8, 2H), 6.81 (s, 2H), 8.03 (t, J=5.8 Hz, 1H), 8.90 (s, 2H).

$t_R$ 1.22 min, MS (ESI) m/z 226.1 [M+H] (100%)

Intermediate 19:
3,4,5-trihydroxy-N-isopropylbenzamide

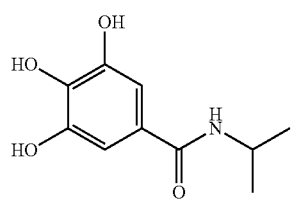

Following synthetic procedure D, isopropylamine (0.234 g, 3.96 mmol) was used to afford the intermediate 5-(isopropylcarbamoyl)benzene-1,2,3-triyl triacetate (10) (0.82 g, 2.431 mmol, yield: 92%), which was deacetylated to obtain the desired 3,4,5-trihydroxy-N-isopropylbenzamide (0.482 g, 2.28 mmol) as a yellow, viscous oil. (Yield: 94%)

$^1$H NMR (400 MHz, DMSO-$d_6$) δ 1.11 (d, J=6.6 Hz, 6H), 1.17 (t, J=7.1 Hz, 1H), 6.81 (s, 2H), 7.79 (d, J=7.9 Hz, 1H), 8.58 (s, 1H), 8.95 (s, 2H).

$t_R$ 1.18 min, MS (ESI) m/z 212.1 [M+H] (100%)

Intermediate 20:
3,4,5-trihydroxy-N-phenylbenzamide

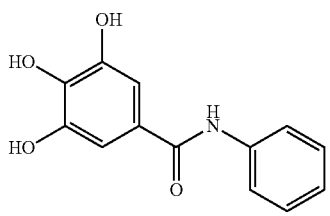 [SMILES: O=C(Nc1ccccc1)c1cc(O)c(O)c(O)c1]

Following synthetic procedure D, aniline (0.444 g, 4.77 mmol) was used to afford the intermediate 5-(phenylcarbamoyl)benzene-1,2,3-triyl triacetate (11) (1.28 g, 3.45 mmol, yield: 72%), which was deacetylated to obtain the desired 3,4,5-trihydroxy-N-phenylbenzamide (0.635 g, 2.59 mmol) as a yellow, viscous oil. (Yield: 75%)

$^1$H NMR (400 MHz, DMSO-$d_6$) δ 6.94 (s, 2H) 7.00-7.07 (m, 1H), 7.26-7.35 (m, 2H), 7.70-7.77 (m, 2H), 9.05 (s, 2H), 9.88 (s, 1H).

$t_R$ 1.29 min, MS (ESI) m/z 246.0 [M+H] (100%)

Intermediate 21:
N-benzyl-3,4,5-trihydroxybenzamide

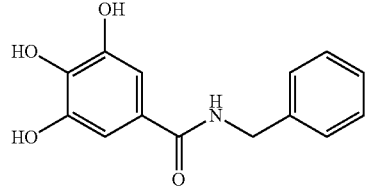 [SMILES: O=C(NCc1ccccc1)c1cc(O)c(O)c(O)c1]

Following synthetic procedure D, benzylamine (0.358 g, 3.34 mmol) was used to afford the intermediate 5-(benzylcarbamoyl)benzene-1,2,3-triyl triacetate (12) (0.857 g, 2.225 mmol, yield: 100%), which was deacetylated to obtain the desired N-benzyl-3,4,5-trihydroxybenzamide (0.525 g, 2.024 mmol) white solid. (Yield: 91%)

$^1$H NMR (400 MHz, DMSO-$d_6$) δ 4.39 (d, J=6.0 Hz, 2H) 6.86 (s, 2H), 7.18-7.33 (m, 5H), 8.62 (t, J=6.0 Hz, 1H), 8.97 (s, 2H).

$t_R$ 1.28 min, MS (ESI) m/z 260.0 [M+H] (100%)

Synthetic Procedure E

In 50 mL of the alcohol of interest, 3,4,5-trihydroxybenzoic acid (1) (1.5 g, 8.85 mmol) was dissolved, followed by addition of 10 drops of sulfuric acid. The solution was refluxed overnight. Afterwards, the solution was allowed to cool to room temperature. The residual alcohol was evaporated, yielding the gallic acid ester derivatives 22, 23, 24 as a solid compound.

Intermediate 22: Ethyl 3,4,5-trihydroxybenzoate

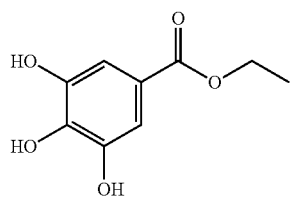

Following synthetic procedure E, ethanol was used for synthesis of the desired ethyl 3,4,5-trihydroxybenzoate (0.600 g, 4.556 mmol), which was obtained as a white solid. (Yield: 51.5%)

$^1$H NMR (400 MHz, DMSO-$d_6$) δ 1.26 (t, J=7.1 Hz, 3H), 4.20 (q, J=7.1 Hz, 2H), 6.94 (s, 2H), 9.16 (s, 3H).

$t_R$ 0.86 min, MS (ESI) m/z 395.5 [2M–H] (100%)

Intermediate 23: Propyl 3,4,5-trihydroxybenzoate

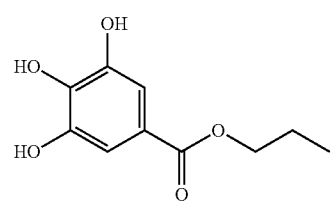

Following synthetic procedure E, propan-1-ol was used for synthesis of propyl 3,4,5-trihydroxybenzoate (1.416 g, 7.17 mmol). (Yield: 81%)

$^1$H NMR (400 MHz, DMSO-d$_6$) δ 0.93 (t, J=7.4 Hz, 3H). 1.57-1.72 (m, 2H), 4.10 (t, J=6.5 Hz, 2H), 6.95 (s, 2H), 7.44 (d, J=28.2 Hz, 3H).

t$_R$ 1.29 min, MS (ESI) m/z 213.1 [M+H] (95%)

Intermediate 24: Butyl 3,4,5-trihydroxybenzoate

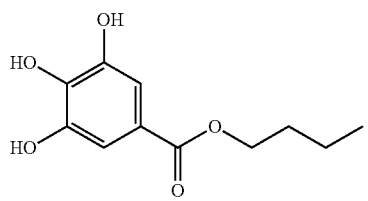 [SMILES: CCCCOC(=O)c1cc(O)c(O)c(O)c1]

Following synthetic procedure E, n-butanol was used for synthesis of butyl 3,4,5-trihydroxybenzoate (6.14 g, 27.1 mmol). (Yield: 92%)

$^1$H NMR (400 MHz, DMSO-d$_6$) δ 0.92 (t, J=7.4 Hz, 3H), 1.29-1.47 (m, 2H), 1.64 (dt, J=6.5, J'=6.5 Hz, 2H), 4.16 (t, J=6.5 Hz, 2H), 6.94 (s, 2H), 8.94 (s, 1H), 9.26 (s, 2H).

t$_R$ 1.14 min, MS (ESI) m/z 226.3 [M+H] (96%)

Synthetic Procedure F

Gallic acid derivative 13-25 or 3,4,5-trihydroxybenzoic acid (1) (1 eq.) and catechol 26-28 (1 eq.) were dissolved in a mixture of 5 mL acetone and 20 mL water. A solution of potassium iodate (1 eq.) in 20 mL water was added dropwise to the reaction mixture over the course of 1 hour while stirring at room temperature. The mixture was stirred for an extra 1.5 h after addition of the potassium iodate and was then left standing for 30 minutes, allowing the target compound to precipitate. The reaction mixture was filtered and the precipitate was washed 3 times with 1 M HCl. After drying under high vacuum, the desired benzotropolone 29-47 was obtained. If necessary, further purification steps were executed.

Final Compound 29: 2-fluoro-3,4,6-trihydroxy-5-oxo-N-phenyl-5H-benzo[7]annulene-8-carboxamide

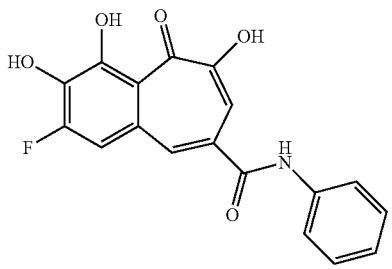 [SMILES: O=C(Nc1ccccc1)c1cc(O)c(=O)c2c(O)c(O)c(F)cc2c1]

Following synthetic procedure F, 3,4,5-trihydroxy-N-phenylbenzamide (20) (0.240 g, 0.979 mmol) and 3-fluorobenzene-1,2-diol (26) (0.125 g, 0.979 mmol) were used. The desired 2-fluoro-3,4,6-trihydroxy-5-oxo-N-phenyl-5H-benzo[7]annulene-8-carboxamide (0.087 g, 0.255 mmol) was obtained as an amorphous powder. (Yield: 26%)

$^1$H NMR (400 MHz, DMSO-d$_6$) δ 1.91 (s, 1H), 2.50 (dt, J=3.6, J'=1.8 Hz, 1H), 3.42 (s, 1H), 7.12 (dd, J=11.6, J'=4.2 Hz, 1H), 7.40-7.34 (m, 1H), 7.49 (d, J=1.5 Hz, 1H), 7.64 (d, J=12.5 Hz, 1H), 7.76-7.71 (m, 1H), 8.05 (d, J=1.2 Hz, 1H), 9.93 (s, 1H), 10.49 (s, 1H), 10.59 (s, 1H), 15.26 (d, J=1.3 Hz, 1H). $^{13}$C NMR (101 MHz, DMSO-d$_6$) δ 112.23, 112.43, 116.12, 117.83, 120.21, 123.88, 128.69, 130.88, 134.21, 139.04, 153.94, 154.28, 154.71, 166.57, 184.00.

t$_R$ 1.77 min, MS (ESI) m/z 340.6 [M−H] (100%)

Final Compound 30: 2-fluoro-3,4,6-trihydroxy-N,N-dimethyl-5-oxo-5H-benzo[7]annulene-8-carboxamide

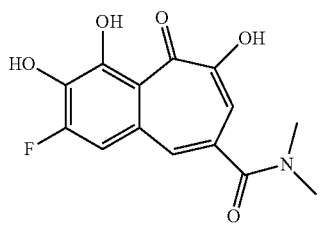 [SMILES: CN(C)C(=O)c1cc(O)c(=O)c2c(O)c(O)c(F)cc2c1]

Following synthetic procedure F, 3,4,5-trihydroxy-N,N-dimethylbenzamide (17) (0.591 g, 3.000 mmol) and 3-fluorobenzene-1,2-diol (26) (0.384 g, 3.00 mmol) were used, but almost no target compound could be found in the precipitate. Instead, the obtained filtrate was extracted with 3×20 mL EtOAc. The organic layers were pooled and then extracted with 0.5 M HCl. The waterphase was then lyophilized. The crude lyophilisate was purified using flash chromatography on C18 gel using MeOH/H$_2$O (0-100% MeOH gradient) as eluent. After lyophilisation of the pooled pure fractions, the desired 2-fluoro-3,4,6-trihydroxy-N,N-dimethyl-5-oxo-5H-benzo[7]annulene-8-carboxamide (0.010 g, 0.034 mmol) was obtained as an amorphous powder. (Yield: 1.38%)

$^1$H NMR (400 MHz, DMSO-d$_6$) δ 3.17 (s, 6H), 4.03 (q, J=7.1 Hz, 1H), 7.29 (s, 1H), 8.28 (d, J=1.9 Hz, 1H). $^{13}$C NMR (101 MHz, DMSO-d$_6$) δ 28.82, 106.91, 107.02, 107.07, 109.27, 110.88, 131.90, 133.63, 140.30, 142.93, 145.61, 159.62, 183.05.

t$_R$ 1.22 min, MS (ESI) m/z 587.5 [M−H] (100%)

Final Compound 31: 2-fluoro-3,4,6-trihydroxy-5-oxo-5H-benzo[7]annulene-8-carboxamide

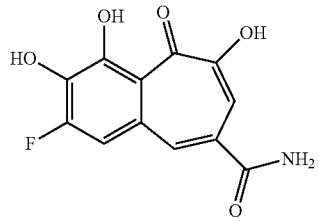 [SMILES: NC(=O)c1cc(O)c(=O)c2c(O)c(O)c(F)cc2c1]

Following synthetic procedure F, 3,4,5-trihydroxybenzamide (13) (0.700 g, 4.14 mmol) and 3-fluorobenzene-1,2-diol (26) (0.530 g, 4.14 mmol) were used. The desired 2-fluoro-3,4,6-trihydroxy-5-oxo-5H-benzo[7]annulene-8-carboxamide (0.293 g, 1.105 mmol) was obtained as an amorphous powder. (Yield: 27%)

¹H NMR (400 MHz, DMSO-d₆) δ 2.07 (s, 1H), 2.50 (s, 1H), 4.36 (s, 1H), 7.52 (d, J=12.3 Hz, 1H), 7.57 (d, J=1.1 Hz, 1H), 8.08 (s, 1H), 8.17 (s, 1H), 15.24 (s, 1H). ¹³C NMR (101 MHz, DMSO-d₆) δ 112.16, 116.13, 117.83, 129.56, 130.00, 134.18, 135.67, 152.28, 153.96, 154.38, 168.64, 183.85.

$t_R$ 1.19 min, MS (ESI) m/z 264.5 [M−H] (100%)

Final Compound 32: Butyl 2-fluoro-3,4,6-trihydroxy-5-oxo-5H-benzo[7]annulene-8-carboxylate

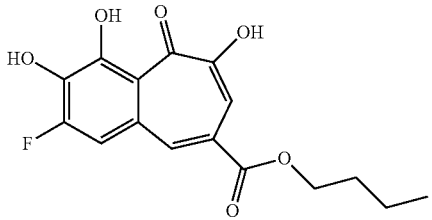 [SMILES: CCCCOC(=O)c1cc(O)c(=O)c2c(O)c(O)c(F)cc2c1]

Following synthetic procedure F, butyl 3,4,5-trihydroxybenzoate (24) (0.583 g, 2.58 mmol) and 3-fluorobenzene-1,2-diol (26) (0.33 g, 2.58 mmol) were used. The desired butyl 2-fluoro-3,4,6-trihydroxy-5-oxo-5H-benzo[7]annulene-8-carboxylate (0.494 g, 1.533 mmol) was obtained as an amorphous powder. (Yield: 60%)

¹H NMR (400 MHz, DMSO-d₆) δ 0.95 (t, J=7.4 Hz, 3H), 1.44 (m, J=14.6, J'=7.4 Hz, 2H), 1.72 (m, J=14.4, J'=6.6 Hz, 2H), 4.30 (t, J=6.6 Hz, 2H), 7.60 (d, J=1.5 Hz, 1H), 7.76 (d, J=12.5 Hz, 1H), 8.28 (d, J=1.1 Hz, 1H), 9.95 (s, 1H), 10.76 (s, 1H), 15.21 (d, J=1.0 Hz, 1H). ¹³C NMR (101 MHz, DMSO-d₆) δ ¹³C NMR (101 MHz, DMSO) δ 13.65, 18.72, 30.16, 65.53, 113.34, 114.86, 117.89, 124.36, 128.95, 129.08, 136.95, 153.96, 165.90, 184.26.

$t_R$ 2.05 min, MS (ESI) m/z 321.5 [M−H] (100%)

Final Compound 33: Propyl 2-chloro-3,4,6-trihydroxy-5-oxo-5H-benzo[7]annulene-8-carboxylate

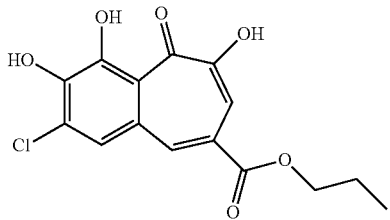 [SMILES: CCCOC(=O)c1cc(O)c(=O)c2c(O)c(O)c(Cl)cc2c1]

Following synthetic procedure F, propyl 3,4,5-trihydroxybenzoate (23) (0.220 g, 1.038 mmol) and 3-chlorobenzene-1,2-diol (27)(0.150 g, 1.038 mmol) were used. The desired propyl 2-chloro-3,4,6-trihydroxy-5-oxo-5H-benzo[7]annulene-8-carboxylate (0.221 g, 0.681 mmol) was obtained as an amorphous powder. (Yield: 66%)

¹H NMR (400 MHz, DMSO-d₆) δ 0.99 (t, J=7.4 Hz, 3H), 1.68-1.81 (m, 2H), 4.25 (t, J=6.6 Hz, 2H), 7.61 (d, J=1.5 Hz, 1H), 7.96 (s, 1H), 8.30 (d, J=0.9 Hz, 1H), 9.96 (s, 1H), 10.80-11.07 (m, 1H), 15.25 (s, 1H). ¹³C NMR (101 MHz, DMSO-d₆) δ 10.39, 21.52, 67.23, 115.22, 118.93, 124.13, 126.47, 127.11, 128.51, 137.51, 144.58, 152.19, 153.84, 165.84, 184.59.

$t_R$ 1.99 min, MS (ESI) m/z 325.0 [M+H] (100%)

Final Compound 34: Butyl 2-chloro-3,4,6-trihydroxy-5-oxo-5H-benzo[7]annulene-8-carboxylate

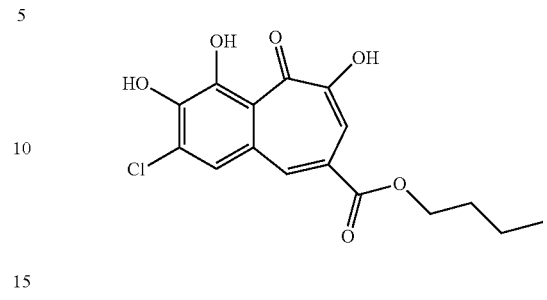

Following synthetic procedure F, butyl 3,4,5-trihydroxybenzoate (24) (0.313 g, 1.384 mmol) and 3-chlorobenzene-1,2-diol (0.2 g, 1.384 mmol) were used. The desired butyl 2-chloro-3,4,6-trihydroxy-5-oxo-5H-benzo[7]annulene-8-carboxylate (0.163 g, 0.995 mmol) was obtained as an amorphous powder. (Yield: 72%).

¹H NMR (400 MHz, DMSO-d₆) δ 0.95 (t, J=7.4 Hz, 3H), 1.44 (dq, J=14.6, J'=7.4 Hz, 2H), 1.67-1.77 (m, 2H), 4.30 (t, J=6.6 Hz, 2H), 7.60 (d, J=1.5 Hz, 1H), 7.95 (s, 1H), 8.28 (d, J=0.9 Hz, 1H), 9.97 (s, 1H), 10.95 (s, 1H), 15.19 (d, J=56.4 Hz, 1H). ¹³C NMR (101 MHz, DMSO-d₆) δ 13.65, 18.73, 30.15, 65.51, 115.24, 118.96, 124.15, 126.48, 127.12, 128.52, 137.54, 144.59, 152.19, 153.86, 165.86, 184.61.

$t_R$ 2.11 min, MS (ESI) m/z 339.1 [M+H] (100%)

Final Compound 35: N-butyl-2-chloro-3,4,6-trihydroxy-5-oxo-5H-benzo[7]annulene-8-carboxamide

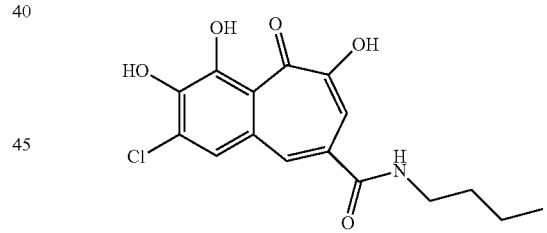

Following synthetic procedure F, N-butyl-3,4,5-trihydroxybenzamide (16) (0.234 g, 1.038 mmol) and 3-chlorobenzene-1,2-diol (0.150 g, 1.038 mmol) were used. The desired N-butyl-2-chloro-3,4,6-trihydroxy-5-oxo-5H-benzo[7]annulene-8-carboxamide (0.163 g, 0.483 mmol) was obtained as an amorphous powder. (Yield: 47%)

¹H NMR (400 MHz, DMSO-d₆) δ 0.91 (t, J=7.3 Hz, 3H), 1.35 (dd, J=15.0, J'=7.3 Hz, 2H), 1.51 (dd, J=14.6, J'=7.3 Hz, 2H), 3.25 (dd, J=12.5, J'=6.1 Hz, 2H), 7.51 (s, 1H), 7.74 (s, 1H), 7.94 (s, 1H), 8.56 (s, 1H), 9.85 (s, 1H), 10.70 (s, 1H), 15.30 (s, 1H). ¹³C NMR (101 MHz, DMSO-d₆) δ 13.78, 19.70, 31.08, 116.63, 118.47, 125.77, 126.60, 129.49, 130.11, 133.73, 143.41, 151.96, 154.07, 166.95, 184.25.

$t_R$ 1.69 min, MS (ESI) m/z 338.1 [M+H] (100%)

Final Compound 36: 2-bromo-3,4,6-trihydroxy-5-oxo-5H-benzo[7]annulene-8-carboxylic acid

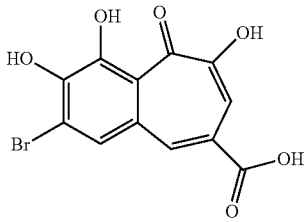 [SMILES: O=C(O)c1cc(O)c(=O)c2c(O)c(O)c(Br)cc2c1]

Following synthetic procedure F, 3,4,5-trihydroxybenzoic acid (1) (0.297 g, 1.746 mmol) and 3-bromobenzene-1,2-diol (28) (0.330 g, 1.746 mmol) were used. The crude solid was further purified by flash chromatography on silica gel using EtOAc/heptane (1:3)+0.1% FA as eluent. The pure fractions were pooled and the desired 2-bromo-3,4,6-trihydroxy-5-oxo-5H-benzo[7]annulene-8-carboxylic acid (0.103 g, 0.315 mmol) was obtained as an amorphous powder. (Yield: 18%)

$^1$H NMR (400 MHz, DMSO-$d_6$) δ 7.66 (d, J=1.5 Hz, 1H), 8.05 (s, 1H), 8.31 (d, J=0.9 Hz, 1H), 9.88 (s, 1H), 10.86 (s, 1H), 13.43 (s, 1H), 15.31 (s, 1H). $^{13}$C NMR (101 MHz, DMSO-$d_6$) δ 116.00, 116.77, 119.34, 124.90, 129.12, 129.86, 137.55, 145.49, 151.49, 153.73, 167.41, 184.71.

$t_R$ 1.50 min, MS (ESI) m/z 325.3 [M−H] (100%)

Final Compound 37: Methyl 2-bromo-3,4,6-trihydroxy-5-oxo-5H-benzo[7]annulene-8-carboxylate

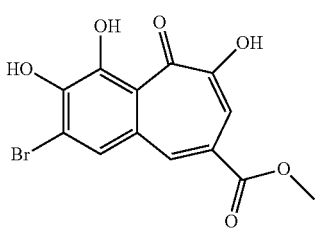 [SMILES: COC(=O)c1cc(O)c(=O)c2c(O)c(O)c(Br)cc2c1]

Following synthetic procedure F, methyl 3,4,5-trihydroxybenzoate (25) (0.300 g, 1.629 mmol) and 3-bromobenzene-1,2-diol (28) (0.308 g, 1.629 mmol) were used. The desired methyl 2-bromo-3,4,6-trihydroxy-5-oxo-5H-benzo[7]annulene-8-carboxylate (0.454 g, 1.331 mmol) was obtained as an amorphous powder. (Yield: 82%)

$^1$H NMR (400 MHz, DMSO-$d_6$) δ 3.88 (s, 3H), 7.63 (d, J=1.5 Hz, 1H), 8.08 (s, 1H), 8.24-8.36 (s, 1H), 9.95 (s, 1H), 10.97 (s, 1H), 15.27 (s, 1H). $^{13}$C NMR (101 MHz, DMSO-$d_6$) δ 53.03, 115.31, 116.75, 119.23, 123.82, 128.83, 130.10, 137.62, 145.76, 151.52, 153.86, 166.36, 184.73.

$t_R$ 1.98 min, MS (ESI) m/z 340.8 [M−H] (93%)

Final Compound 38: Ethyl 2-bromo-3,4,6-trihydroxy-5-oxo-5H-benzo[7]annulene-8-carboxylate

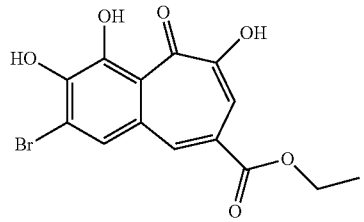 [SMILES: CCOC(=O)c1cc(O)c(=O)c2c(O)c(O)c(Br)cc2c1]

Following synthetic procedure F, ethyl 3,4,5-trihydroxybenzoate (22) (0.210 g, 1.058 mmol) and 3-bromobenzene-1,2-diol (28) (0.308 g, 1.629 mmol) were used. The desired ethyl 2-bromo-3,4,6-trihydroxy-5-oxo-5H-benzo[7]annulene-8-carboxylate (0.256 g, 0.721 mmol) was obtained as an amorphous powder. (Yield: 68%)

$^1$H NMR (400 MHz, DMSO-$d_6$) δ 1.35 (t, J=7.1 Hz, 3H), 4.33 (q, J=7.1 Hz, 2H), 7.61 (d, J=1.5 Hz, 1H), 8.09 (s, 1H), 8.30 (d, J=0.9 Hz, 1H), 9.94 (s, 1H), 10.96 (s, 1H), 15.27 (s, 1H). $^{13}$C NMR (101 MHz, DMSO-$d_6$) δ 14.09, 61.83, 115.36, 116.77, 119.27, 124.10, 128.89, 130.09, 137.57, 145.72, 151.52, 153.86, 165.84, 184.75.

$t_R$ 1.92 min, MS (ESI) m/z 355.0 [M−H] (91%)

Final Compound 39: Propyl 2-bromo-3,4,6-trihydroxy-5-oxo-5H-benzo[7]annulene-8-carboxylate

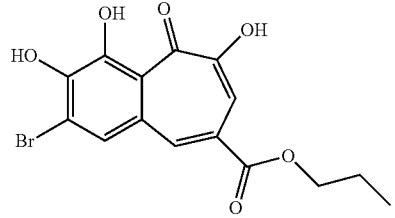 [SMILES: CCCOC(=O)c1cc(O)c(=O)c2c(O)c(O)c(Br)cc2c1]

Following synthetic procedure F, propyl 3,4,5-trihydroxybenzoate (23) (0.168 g, 0.794 mmol) and 3-bromobenzene-1,2-diol (28) (0.150 g, 0.794 mmol) were used. The desired propyl 2-bromo-3,4,6-trihydroxy-5-oxo-5H-benzo[7]annulene-8-carboxylate (0.198 g, 0.536 mmol) was obtained as an amorphous powder. (Yield: 68%)

$^1$H NMR (400 MHz, DMSO-$d_6$) δ 0.99 (t, J=7.4 Hz, 3H), 1.69-1.83 (m, 2H), 4.25 (t, J=6.6 Hz, 2H), 7.62 (d, J=1.5 Hz, 1H), 8.10 (s, 1H), 8.29 (d, J=0.9 Hz, 1H), 9.95 (s, 1H), 10.96 (s, 1H), 15.27 (s, 1H). $^{13}$C NMR (101 MHz, DMSO-$d_6$) δ 10.40, 21.53, 67.23, 115.30, 116.76, 119.24, 124.05, 128.85, 130.10, 137.54, 145.72, 151.52, 153.85, 165.86, 184.73.

$t_R$ 2.02 min, MS (ESI) m/z 371.0 [M+2H] (90%)

Final Compound 40: Butyl 2-bromo-3,4,6-trihydroxy-5-oxo-5H-benzo[7]annulene-8-carboxylate

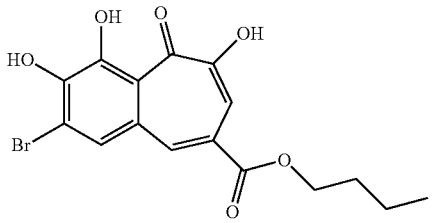

Following synthetic procedure F, butyl 3,4,5-trihydroxybenzoate (24) (0.395 g, 1.746 mmol) and 3-bromobenzene-1,2-diol (28) (0.33 g, 1.746 mmol) were used to afford the desired butyl 2-bromo-3,4,6-trihydroxy-5-oxo-5H-benzo[7]annulene-8-carboxylate (0.349 g, 0.911 mmol) as an amorphous powder. (Yield: 52%)

$^1$H NMR (400 MHz, DMSO-d$_6$) δ 0.95 (t, J=7.4 Hz, 3H). 1.44 (m, J=14.6, J'=7.4 Hz, 2H), 1.77-1.68 (m, 2H), 4.29 (t, J=6.6 Hz, 2H), 7.60 (d, J=1.4 Hz, 1H), 8.08 (s, 1H), 8.27 (s, 1H), 9.94 (s, 1H), 10.94 (s, 1H), 15.26 (s, 1H). $^{13}$C NMR (101 MHz, DMSO-d$_6$) δ 13.65, 18.72, 30.14, 65.51, 115.31, 116.77, 119.27, 124.08, 128.87, 130.10, 137.55, 145.73, 151.52, 153.87, 165.89, 184.76.

t$_R$ 2.20 min, MS (ESI) m/z 381.5 [M−H] (100%)

Final Compound 41: 2-bromo-3,4,6-trihydroxy-5-oxo-5H-benzo[7]annulene-8-carboxamide

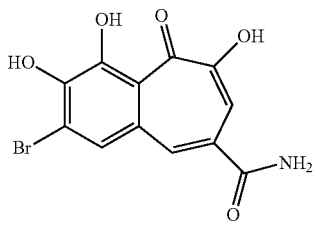 [SMILES: NC(=O)c1cc(O)c(=O)c2c(O)c(O)c(Br)cc2c1]

Following general procedure C, 3,4,5-trihydroxybenzamide (13) (0.483 g, 2.86 mmol) and 3-bromobenzene-1,2-diol (28) (0.540 g, 2.86 mmol) were used. The obtained precipitate was suspended in methanol and filtered. The filtrate was evaporated to give the desired 2-bromo-3,4,6-trihydroxy-5-oxo-5H-benzo[7]annulene-8-carboxamide (0.798 g, 2.447 mmol) as a pure powder. (Yield: 85%)

$^1$H NMR (400 MHz, DMSO-d$_6$) δ 7.55 (s, 1H), 7.60 (d, J=2.2 Hz, 1H), 7.87 (s, 1H), 8.00-8.09 (m, 2H), 9.81 (s, 1H), 10.74 (s, 1H), 15.32 (s, 1H). $^{13}$C NMR (101 MHz, DMSO-d$_6$) δ 116.64, 116.83, 119.22, 128.84, 129.24, 129.75, 134.17, 144.65, 151.32, 153.92, 168.57, 184.37.

t$_R$: 1.21, MS (ESI) m/z 324.3 [M−H]. (100%)

Final Compound 42: 2-bromo-N-ethyl-3,4,6-trihydroxy-5-oxo-5H-benzo[7]annulene-8-carboxamide

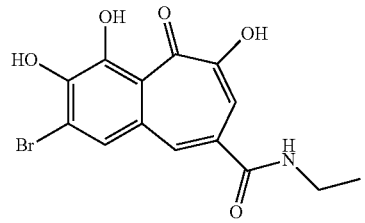 [SMILES: CCNC(=O)c1cc(O)c(=O)c2c(O)c(O)c(Br)cc2c1]

Following synthetic procedure F, N-ethyl-3,4,5-trihydroxybenzamide (14) (0.270 g, 1.369 mmol) and 3-bromobenzene-1,2-diol (28) (0.259 g, 1.369 mmol) were used. The desired 2-bromo-N-ethyl-3,4,6-trihydroxy-5-oxo-5H-benzo[7]annulene-8-carboxamide (0.302 g, 0.853 mmol) was obtained as an amorphous powder. (Yield: 62%).

$^1$H NMR (400 MHz, DMSO-d$_6$) δ 1.16-1.10 (m, 3H), 7.52 (d, J=1.4 Hz, 2H), 7.89 (s, 1H), 7.95 (s, 1H), 8.59 (t, J=5.3 Hz, 1H), 9.86 (s, 1H), 10.76 (s, 1H), 15.31 (s, 1H). $^{13}$C NMR (101 MHz, DMSO-d$_6$) δ 14.56, 34.65, 116.61, 116.86, 119.09, 128.74, 129.76, 129.86, 133.66, 144.53, 151.27, 154.03, 166.72, 184.32.

t$_R$ 1.48 min, MS (ESI) m/z 356.0 [M+2H] (100%)

Final Compound 43: 2-bromo-3,4,6-trihydroxy-5-oxo-N-propyl-5H-benzo[7]annulene-8-carboxamide

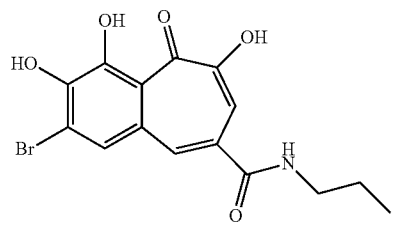 [SMILES: CCCNC(=O)c1cc(O)c(=O)c2c(O)c(O)c(Br)cc2c1]

Following synthetic procedure F, 3,4,5-trihydroxy-N-propylbenzamide (15) (0.240 g, 1.136 mmol) and 3-bromobenzene-1,2-diol (28) (0.215 g, 1.136 mmol) were used. The desired 2-bromo-3,4,6-trihydroxy-5-oxo-N-propyl-5H-benzo[7]annulene-8-carboxamide (0.163 g, 0.709 mmol) was obtained as an amorphous powder. (Yield: 62%)

$^1$H NMR (400 MHz, DMSO-d$_6$) δ 0.91 (t, J=7.4 Hz, 3H), 1.54 (dt, J=14.4, J'=7.2 Hz, 2H), 3.22 (dd, J=12.9, J'=6.8 Hz, 2H), 7.53 (d, J=1.4 Hz, 1H), 7.95 (s, 1H), 7.89 (s, 1H), 8.57 (t, J=5.5 Hz, 1H), 9.84 (s, 1H), 10.72 (s, 1H), 15.31 (s, 1H). $^{13}$C NMR (101 MHz, DMSO-d$_6$) δ 11.52, 22.22, 41.55, 116.61, 116.86, 119.02, 128.71, 129.72, 129.93, 133.65, 144.10, 150.88, 154.03, 166.94, 184.33.

t$_R$ 1.62 min, MS (ESI) m/z 268.0 [M] (95%)

Final Compound 44: 2-bromo-N-butyl-3,4,6-trihydroxy-5-oxo-5H-benzo[7]annulene-8-carboxamide

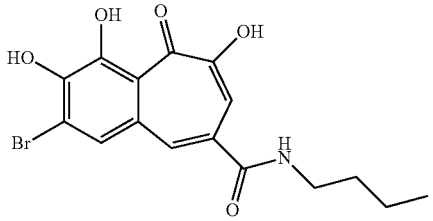

Following synthetic procedure F, N-butyl-3,4,5-trihydroxybenzamide (16) (0.238 g, 1.058 mmol) and 3-bromobenzene-1,2-diol (28) (0.200 g, 1.058 mmol) were used. The desired 2-bromo-N-butyl-3,4,6-trihydroxy-5-oxo-5H-benzo[7]annulene-8-carboxamide (0.174 g, 0.455 mmol) was obtained as an amorphous powder. (Yield: 43%)

$^1$H NMR (400 MHz, DMSO-d$_6$) δ 0.91 (t, J=7.3 Hz, 3H). 1.36 (dt, J=14.6, J'=7.2 Hz, 2H), 1.47-1.56 (m, 2H), 3.25 (dd, J=12.7, J'=6.9 Hz, 2H), 7.52 (d, J=1.4 Hz, 1H), 7.89 (s, 1H), 7.94 (s, 1H), 8.56 (t, J=5.5 Hz, 1H), 9.85 (s, 1H), 10.74 (s, 1H), 15.32 (s, 1H). $^{13}$C NMR (101 MHz, DMSO-d$_6$) δ 13.74, 19.67, 31.05, 116.64, 116.86, 118.94, 128.74, 129.76, 129.93, 133.64, 144.51, 151.27, 154.03, 166.89, 184.32.

$t_R$ 1.74 min, MS (ESI) m/z 382.0 [M] (100%)

Final compound 45: 2-bromo-3,4,6-trihydroxy-N-isopropyl-5-oxo-5H-benzo[7]annulene-8-carboxamide

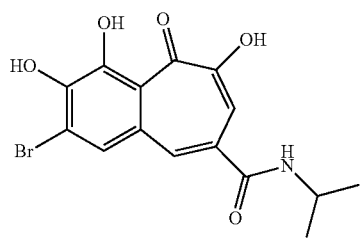 [SMILES: CC(C)NC(=O)c1cc(O)c(=O)c2c(O)c(O)c(Br)cc2c1]

Following synthetic procedure F, 3,4,5-trihydroxy-N-isopropylbenzamide (19) (0.750 g, 3.55 mmol) and 3-bromobenzene-1,2-diol (28) (0.540 g, 2.86 mmol) were used. After execution of general washing steps, the crude product was washed several times with small amounts of hexane and the desired 2-bromo-3,4,6-trihydroxy-N-isopropyl-5-oxo-5H-benzo[7]annulene-8-carboxamide (0.692 g, 1.880 mmol) was obtained as an amorphous powder. (Yield: 53%)

$^1$H NMR (400 MHz, DMSO-ds) δ 1.17 (t, J=6.6 Hz, 6H), 4.01-4.09 (m, 1H), 7.53 (d, J=1.4 Hz, 1H), 7.91 (s, 1H), 7.94 (d, J=0.9 Hz, 1H), 8.37 (d, J=7.6 Hz, 1H), 9.81-9.83 (m, 1H), 10.71 (s, 1H), 15.32 (s, 1H). $^{13}$C NMR (101 MHz, DMSO-ds) δ 22.26, 39.52, 41.29, 116.82, 119.16, 128.73, 129.91, 130.04, 133.66, 144.50, 151.29, 154.01, 166.09, 184.32.

$t_R$ 1.65 min, MS (ESI) m/z 368.4 [M] (94%)

Final Compound 46: N-benzyl-2-bromo-3,4,6-trihydroxy-5-oxo-5H-benzo[7]annulene-8-carboxamide

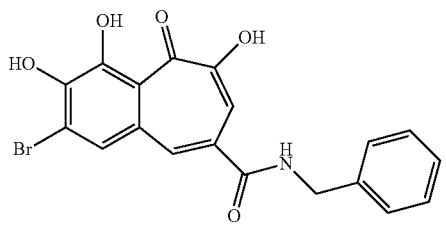 [SMILES: O=C(NCc1ccccc1)c1cc(O)c(=O)c2c(O)c(O)c(Br)cc2c1]

Following synthetic procedure F, N-benzyl-3,4,5-trihydroxybenzamide (21) (0.274 g, 1.058 mmol) and 3-bromobenzene-1,2-diol (28) (0.200 g, 1.058 mmol) were used. The desired N-benzyl-2-bromo-3,4,6-trihydroxy-5-oxo-5H-benzo[7]annulene-8-carboxamide (0.312 g, 0.750 mmol) was obtained as an amorphous powder. (Yield: 71%)

$^1$H NMR (400 MHz, DMSO-d$_6$) δ 4.48 (s, 2H), 7.35 (s, 5H), 7.57 (s, 1H), 7.90 (s, 1H), 8.04 (s, 1H), 9.16 (s, 1H), 9.88 (s, 1H), 10.77 (s, 1H), 15.32 (s, 1H). $^{13}$C NMR (101 MHz, DMSO-d$_6$) δ 43.21, 116.51, 116.63, 118.75, 126.85, 127.33, 128.33, 128.77, 129.39, 129.58, 133.88, 139.20, 144.33, 150.87, 154.05, 166.99, 183.56.

$t_R$ 1.76 min, MS (ESI) m/z 416.1 [M] (100%)

Final Compound 47: 2-bromo-3,4,6-trihydroxy-N-isobutyl-5-oxo-5H-benzo[7]annulene-8-carboxamide

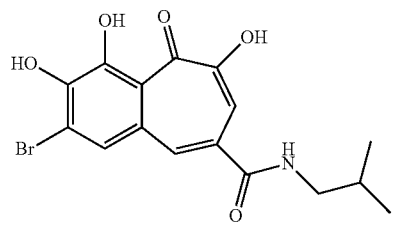 [SMILES: CC(C)CNC(=O)c1cc(O)c(=O)c2c(O)c(O)c(Br)cc2c1]

Following synthetic procedure F, 3,4,5-trihydroxy-N-isobutylbenzamide (18) (0.280 g, 1.243 mmol) and 3-bromobenzene-1,2-diol (28) (0.235 g, 1.243 mmol) were used. The desired 2-bromo-3,4,6-trihydroxy-N-isobutyl-5-oxo-5H-benzo[7]annulene-8-carboxamide (0.034 g, 0.089 mmol) was obtained as an amorphous powder. (Yield: 7%).

$^1$H NMR (400 MHz, DMSO-d$_6$) δ 0.91 (d, J=6.6 Hz, 6H), 1.79-1.89 (m, 1H), 3.08 (t, J=6.2 Hz, 2H), 7.52 (s, 1H), 7.92 (d, J=18.7 Hz, 2H), 8.59 (s, 1H), 9.86 (s, 1H), 10.73 (s, 1H), 15.33 (s, 1H). $^{13}$C NMR (101 MHz, DMSO-d$_6$) δ 20.25, 28.02, 47.24, 116.71, 116.84, 119.13, 128.74, 129.65, 129.99, 133.61, 144.48, 151.25, 154.01, 167.09, 184.31.

$t_R$ 1.93 min, MS (ESI) m/z 381.9 [M–H] (100%)

Synthesized compounds of the invention include:
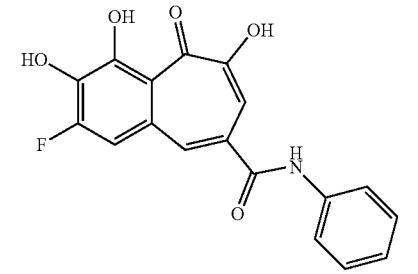
29
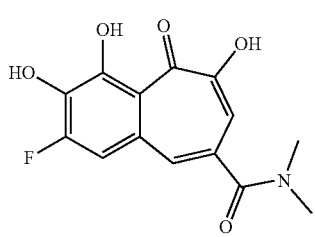
30
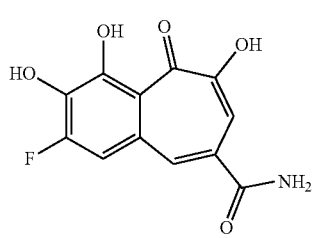
31
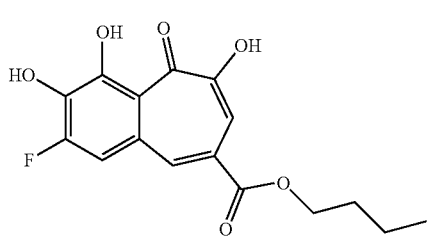
32
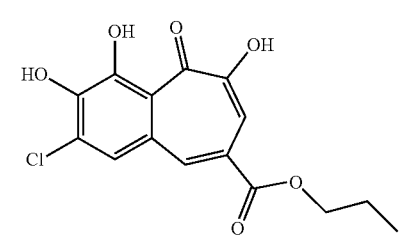
33
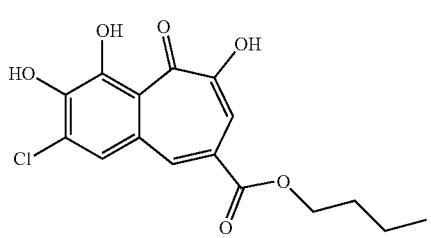
34
-continued
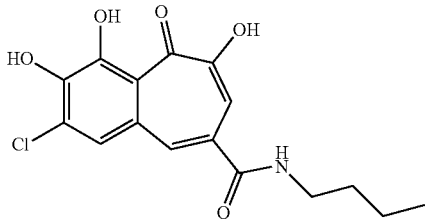
35
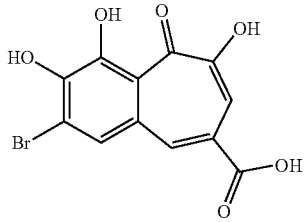
36
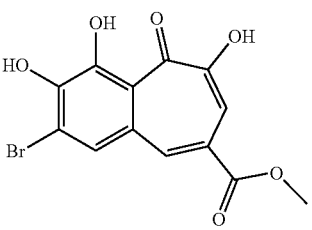
37
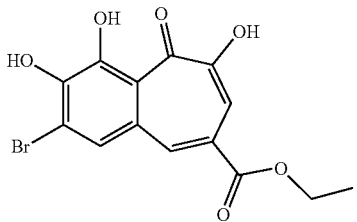
38
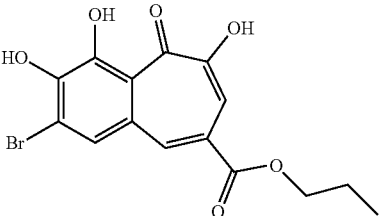
39
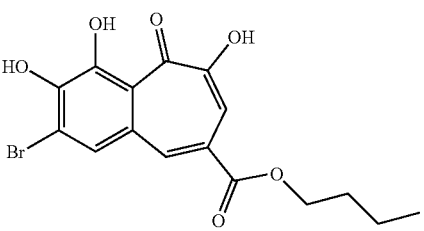
40
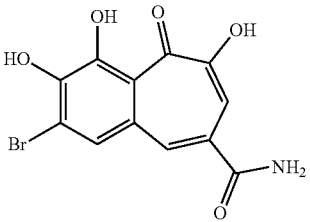
41

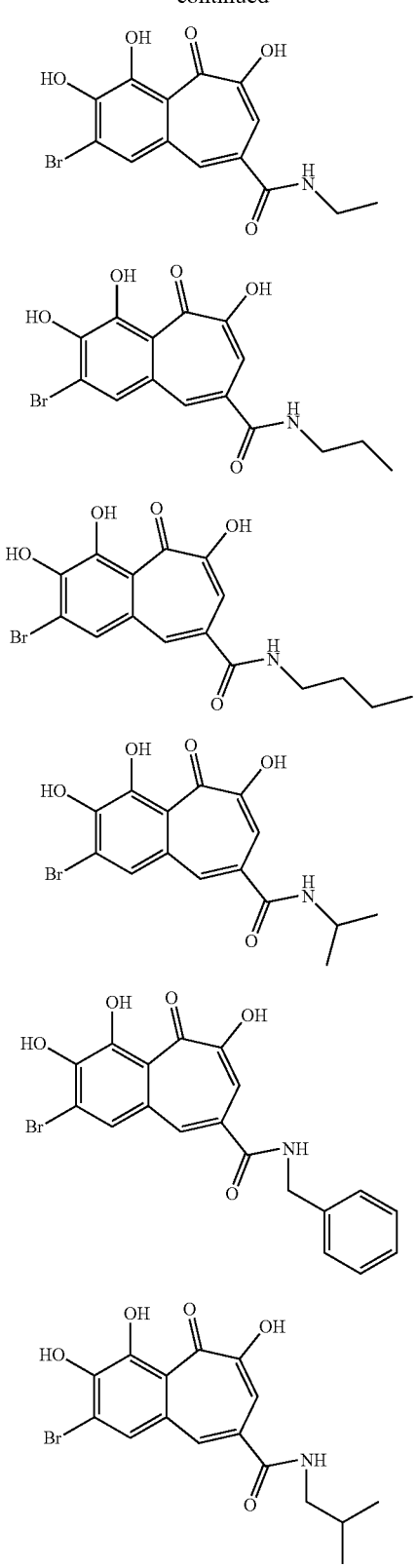

Biochemical Evaluation

Final compounds were screened for autophagy/Atg4B inhibition in 3 different assays: a gel-based screening for Atg4B inhibition, a CYTO-ID-based phenotypical screening for autophagy inhibition and a luciferase reporter assay for assessment of intracellular Atg4B inhibition. Initially, all compounds were evaluated using the SDS-PAGE-based screening assay. Each test compound was incubated with [LC3B-GST], a fusion protein of LC3B and glutathione-S-transferase, and Atg4B in Tris-HCl buffer for a fixed time period. Afterwards, residual fusion protein and cleavage products were separated by gel electrophoresis and quantified using optical densitometry. Based on the % of uncleaved substrate, compound activity was expressed as % enzyme inhibition at 500 µM compound concentration. A set of compounds was then subjected to a CYTO ID-based assay (Stankov et al., 2014). This assay is based on selective labelling of autophagic vacuoles in Jurkat T-cells. Quantification of the stained autophagic compartments can then be used for assessment of autophagy modulation. Autophagy induction was obtained by addition of 10 µM everolimus in EtOH in the presence of 10 µM test compound and autophagy inhibition was monitored as a decline in autophagic vacuoles and the corresponding fluorescent signal. Eventually, compounds showing notable activity in any of the previous screening assays were examined for in cellulo Atg4B inhibition. Herefore, we used a luciferase reporter assay (Ketteler et al., 2008). This assay is based on the Atg4B-dependent release of the Gaussia luciferase (GLUC) from cells. GLUC is a reporter enzyme secreted from cells upon signal peptide-mediated secretion. However, by absence of the signalling peptide, GLUC is rapidly released from the cell via a non-conventional pathway requiring ER/Golgi-trafficking. By anchoring of dNGLUC, the N-terminally deleted form, to β-actin, release of the enzyme via this pathway can be avoided. Furthermore, insertion of LC3 fused to dNGLUC (β-actin-LC3-GLUC) via a cleavable peptide bond can make dNGLUC secretion dependent of proteolytic cleavage by Atg4B. The secreted dNGLUC is then responsible for the production of a chemiluminescent signal in the presence of the luciferase substrate coelenterazine. Upon addition of an Atg4B-inhibiting substance, cleavage of the fusion protein can be disturbed, resulting in a decreased intensity of the observed signal. Hence, this method allows for indirect detection of intracellular Atg4B activity/inhibition.

Substrate and Enzyme Origin

The LC3B-GST coding sequence was inserted into the pET11a vector (Novagen), and expressed in *Escherichia coli*. The recombinant HsAtg4B enzyme was produced in *Escherichia coli* as GST-HsAtg4B and purified by GST-affinity chromatography. The GST tag was removed with PreScission protease. Enzyme purification was performed as described by Sugawara et al (J. Biol. Chem., 2005).

General SDS-PAGE Assay Procedure

LC3B-GST (2 µg/µL) dissolved in 50 mM Tris pH 8.0, 150 mM NaCl and 1 mM DTT and HsAtg4B (2.34 µg/µL) dissolved in 20 mM Tris pH 7.4, 150 mM NaCl and 2 mM DTT were stored in a −80° C. freezer in small aliquots. For each assay, fresh aliquots of enzyme and substrate were thawn, and fresh buffer was used. All substrate and enzyme dilutions were made in LoBind Eppendorf® tubes. Buffer used in the following methods for making appropriate dilutions consisted of 50 mM Tris-HCl pH 7.4, 150 mM NaCl, 2 mM DTT and 0.1% TWEEN 20, freshly prepared at the day of the experiment. 10 µL of Laemmli Sample Buffer was added to each sample to stop enzymatic cleavage of LC3B-GST and the samples were boiled for 4 minutes. The samples were loaded onto a NuPAGE® Novex 12 Bis-Tris 1.0 mm 15 well gel after termination of the enzymatic reaction. A Thermo-Scientific® PageRuler Prestained Protein Ladder was used as a reference for molecular weights of the separated proteins. Gels were run in a NuPAGE Bolt® Mini Gel Tank for 50 minutes using NuPAGE® MOPS SDS Running Buffer at constant voltage (170V) using a Bio-Rad PowerPac® Basic 300 V Power Supply. Gels were stained for 2 hours using Oriole™ Fluorescent Gel Stain, (purchased from Bio-Rad®), and destained by washing several times with Milli-Q™ water. Lane densities were scanned using a Roche® Lumi-Imager® F1 at a UV max of 600 nm and an exposure time of 500 ms, yielding three clearly visible bands per lane (from top to bottom): uncleaved LC3B-GST, free GST and free LC3B. Lane densities were quantified using Totallab Quant® software.

Protocol for Determination of Atg4B Inhibition Using the SDS-PAGE-Based Screening Assay Compounds were dissolved in DMSO in a 10 mM concentration (final concentration of 500 µM in the assay). Fivefold dilutions of the library compounds were made in buffer. Atg4B and LC3B-GST aliquots were thawn and dilutions were made (Atg4B: 0.625 ng/µL; LC3B-GST: 0.4 µg/µL). To 2.5 µL of LC3B-GST was added 2.5 µL of testing compound. Per gel a maximum of 13 compounds was loaded. A control sample was made consisting of 2.5 µL of substrate dilution and 2.5 µL of buffer solution containing 20% v/v of DMSO (5% in the final mixture). 5 µL of Atg4B was added to each one of the 14 samples and incubated at room temperature for 6 minutes. Reactions were stopped by adding Laemmli sample buffer. Eventually, quantification of both the intact fusion protein and its cleavage products was performed using optical densitometry. The percentage of uncleaved [LC3B-GST] was used as a measure for Atg4B activity, and was calculated using the following formula (OD=Optical Density):

$$\% \text{ uncleaved}[LC3B - GST] = \frac{OD([LC3B - GST])}{OD[(LC3B - GST]) + OD(GST) + OD(LC3B)} \times 100\%$$

The percentage of uncleaved substrate was then used to express the amount of enzyme inhibition as percent inhibition. Herefore, we set the percentage of uncleaved substrate in the control sample as zero percent of inhibition, while 100% of uncleaved substrate corresponded to complete enzyme inhibition.

For this conversion, we applied the following formula:

$$\text{enzyme } inh. \ (\%) = \frac{\text{uncleaved}([LC3B - GST])\text{test sample} - \text{uncleaved}([LC3B - GST])\text{control sample}}{100 - \text{uncleaved}([LC3B - GST])\text{control sample}} \times 100\%$$

In case of a negative percent inhibition (suggesting Atg4B induction), the outcome was set to zero percent.

CYTO-ID-Based Phenotypical Screening for Autophagy Inhibition

Compounds were obtained as a 10 mM stock dissolved in 100% DMSO (Acros Organics, 167850010). Jurkat T-cells were cultured in RPMI 1640 medium (Invitrogen, San Diego, Calif.) supplemented with 10% fetal bovine serum. A total of $1 \times 10^6$ cells was transferred into a standard 12-well plate. Cells were treated with 10 µM everolimus (Novartis Institutes for Biomedical Research, Basel, Switzerland) dissolved in 100% EtOH in the presence of 10 µM of the compound to be tested. A set of controls were incorporated into the experiments: untreated Jurkat T-cells, cells treated with 10 µM everolimus and cells treated with both 10 µM everolimus and 10 mM 3-MA. Following 16 hours of treatment, cells were washed and autophagosomes were stained for 30 minutes with CYTO-ID Green Autophagy Detection Reagent (Enzo Life Sciences Inc., ENZ-51031-K200) according to manufacturer's protocol. Cells were then washed and passed through a flow cytometer (Accuri c6, BD biosciences) to count individual Jurkat T-cells which incorporated the fluorescent CYTO-ID dye.

Luciferase Reporter Assay for Assessment of Intracellular Atg4B Inhibition

Plasmid Transformation and Purification

A pEAK12 plasmid bearing the sequence for a Gaussia luciferase (GLUC) reporter fused to the ATG4 substrate LC3 and ankered in the cell with β-actin (β-actin-LC3-GLUC) was obtained from Dr. Ketteler (R. MRC Laboratory for molecular cell biology, UCL, London, UK). The plasmid was transformed into *E. coli* (One Shot® TOP10 kit, invitrogen, C4040-03) according to standard procedures. After allowing to grow, purification of the plasmid out of a 1 liter culture was performed using Plasmid Maxi kit (Qiagen, 12162).

Transfection

HEK 293T cells were cultured in DMEM medium (Invitrogen, San Diego, Calif.) supplemented with 10% fetal bovine serum. Amaxa Cell Line Nucleofector kit V (Lonza, VCA-1003, USA) was used to transfect $2 \times 10^6$ cells with either 3 µg of the purified pEAK12 plasmid or control plasmid (pmaxGFP®) according to standard procedures. Cells were then transferred to a 24-well plate and incubated at 37° C.

Screening Protocol for in Cellulo Atg4B Inhibition 24 hours post transfection, medium in which HEK 293T cells were cultured was removed and 500 µL fresh serum free RPMI medium was added. The medium contained no treatment, 10 µM everolimus or everolimus+10 µM of the compound to be tested. Cells were incubated for 6 hours after which medium was removed for analysis. BioLux Gaussia Luciferase Assay kit (NEB, E3300 S, UK) was used to measure the luciferase activity. Briefly, 10 µL of the medium was transferred in an opaque 96-well microtiter plate and mixed with 50 µL assay buffer. The luciferase activity was measured after a 5 seconds integration time using the Infinite® 200 Pro microplate reader (Tecan).

Screening Results Overview

Screening results of the benzotropolone library and 3-methyladenine (3-MA), the most widely used reference autophagy inhibitor, are shown in Table 1. Autophagy modulation in the CYTO-ID assay and dNGLUC activity in the luciferase reporter assay were expressed relative to the everolimus-treated group.

TABLE 1
Screening results of the benzotropolone library.
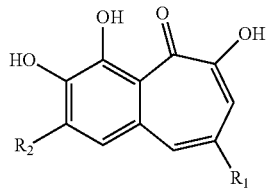
| Compound | R$_1$ | R$_2$ | SDS-PAGE Enzyme inhibition (%) | CYTOID assay[a] | Luciferase reporter assay[b] |
|---|---|---|---|---|---|
| 3-MA[c] | | | — | 0.57[d] | — |
| 29 | -C(O)-NH-Ph | F | 64.78 | 0.97 | N.D.[e] |
| 30 | -C(O)-N(CH$_3$)$_2$ | F | 47.63 | 0.88 | N.D. |
| 31 | -C(O)-NH$_2$ | F | 39.85 | N.D. | N.D. |
| 32 | -C(O)-O-butyl | F | 17.72 | 0.58 | 0.76 |
| 33 | -C(O)-O-propyl | Cl | 24.66 | 0.35 | 0.24 |
| 34 | -C(O)-O-butyl | Cl | 12.46 | 0.29 | 0.18 |
| 35 | -C(O)-NH-butyl | Cl | 32.04 | 0.90 | 0.17 |
| 36 | -C(O)-OH | Br | 19.59 | 0.95 | N.D. |
| 37 | -C(O)-O-CH$_3$ | Br | 30.30 | 0.99 | 0.37 |

TABLE 1-continued

Screening results of the benzotropolone library.

| Compound | R₁ | R₂ | SDS-PAGE Enzyme inhibition (%) | CYTOID assay[a] | Luciferase reporter assay[b] |
|---|---|---|---|---|---|
| 38 | –C(=O)OEt (ethyl ester) | Br | 16.69 | 0.94 | 0.85 |
| 39 | –C(=O)O-propyl | Br | 18.03 | 0.52 | 0.17 |
| 40 | –C(=O)O-butyl | Br | 49.97 | 0.55 | 0.43 |
| 41 | –C(=O)NH₂ | Br | 63.28 | 0.85 | 0.75 |
| 42 | –C(=O)NH-ethyl | Br | 60.17 | 0.94 | 0.18 |
| 43 | –C(=O)NH-propyl | Br | 45.05 | 0.73 | 0.21 |
| 44 | –C(=O)NH-butyl | Br | 33.68 | 0.99 | 1.00 |
| 45 | –C(=O)NH-isopropyl | Br | 65.74 | 0.95 | N.D. |
| 46 | –C(=O)NH-benzyl | Br | 25.97 | 0.60 | 0.21 |

TABLE 1-continued

Screening results of the benzotropolone library.

[Structure: benzotropolone core with OH, HO, O, OH substituents and R1, R2 positions]

| Compound | R₁ | R₂ | SDS-PAGE Enzyme inhibition (%) | CYTOID assay[a] | Luciferase reporter assay[b] |
|---|---|---|---|---|---|
| 47 | [—C(=O)—NH—CH₂—CH(CH₃)₂ group] | Br | 34.38 | 0.85 | 0.29 |

(a) Autophagy in everolimus-treated and control group was respectively 1 (normalized) and 0.37
(b) Luciferase activity in everolimus-treated and control group was respectively 1
(a) Autophagy in everolimus-treated and control group was respectively 1 (normalized) and 0.37
(b) Luciferase activity in everolimus-treated and control group was respectively 1 (normalized) and 0.40
(c) 3-MA: 3-Methyladenine, reference autophagy inhibitor
(d) Compound was tested at 10 mM concentration
(e) "N.D.": Compound was not determined Determination of ADME-Properties
Metabolic Stability in Mouse Microsomes A 5 mM compound solution was prepared in DMSO. A mixture of 713 µL milliQ water (Milli-Q Direct 8, Merck Millipore), 200 µL 0.5 M phosphate buffer (BD Diagnostic Systems, 257385), 50 µL NADPH regenerating system solution A (BD Biosciences), 10 µL NADPH regenerating system solution B (BD Biosciences) and 2 µL compound solution was prepared and heated for 5 min at 37° C. 25 µL of liver microsomes (Corning B.V. Life Sciences) was added to the mixture and 20 µL samples were withdrawn at 0, 15, 30, 60, 120, 240 and 360 minutes. 80 µL (4×20 µL) of cold acetonitrile (Sigma-Aldrich) was added to the samples on ice for 10 minutes. Afterwards, the mixtures were centrifuged at 13000 rpm for 5 minutes at 4° C. A volume of 75 µL of an acetonitrile/water (10/90) mixture was added to 25 µL supernatant and the obtained samples were analyzed by LC-MS/MS in triplicate.

Plasma Stability in Mouse Plasma

A 10 mM compound solution was prepared in DMSO (Acros). A 5 µL aliquot was added to 995 µL of mouse plasma (Non Swiss Albino Mouse Plasma, sodium citrate, DivBioScience, IMS-N) to obtain a final solution of 50 µM. The mixture was gently shaken for 6 hours at 37° C. Aliquots of 100 µL were taken at various time points (0, 30, 60, 120, 180, 360 minutes) and diluted with 400 µL of cold methanol (Sigma-Aldrich) (stored at 4° C.). The suspension was centrifuged at 14000 rpm for 5 minutes. Afterwards, 50 µL of the supernatant was diluted with 950 µL of methanol and analyzed with LC-MS/MS (Waters Acquity H-class UPLC system with ion trap mass spectrometer, Bruker Daltonics Esquire 3000 plus, and Agilent 1100 Series LC system). The samples were analyzed in triplicate. A standard curve was plotted using compound concentrations of 3.12-100 µM in mouse plasma.

Screening Overview ADME-Properties

Figure 2:
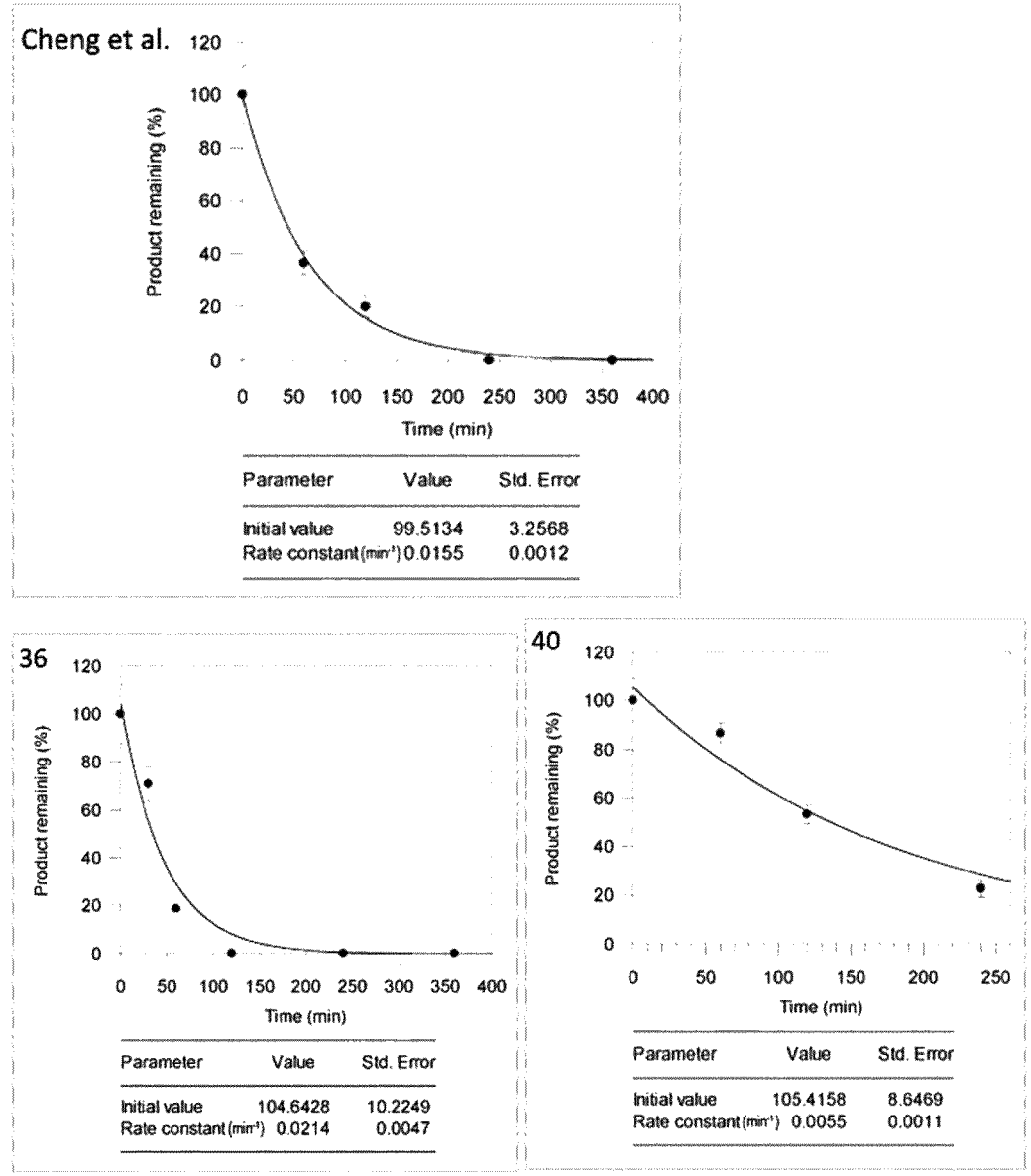
FIG. 2: Stability of compound 36, reference compound (Cheng et al.) and compound 40 in mouse plasma expressed as the % remaining product as a function of time. Error bars are the variation in duplicate measurements. Standard errors are the variations on the fitted curve.

ADME-results were summarized in Table 2. For benchmarking purposes, the non-halogenated benzotropolone reported by Shu et al., as well as a butyl ester, of which the synthetic procedure was reported by Cheng et al., were included. Stability plots are shown in FIG. 1 and FIG. 2.

The carboxylic acids showed higher microsomal stability than their corresponding butyl esters. A substantial increase in plasma stability as well as microsomal stability was observed for the brominated compounds (36, 40) compared to the non-halogenated analogues.

TABLE 2 in vitro ADME-properties of selected compounds.

| Compound | R₁ | R₂ | Microsomal stability (mouse) recovery of parent compound after 30 min (%) | Plasma stability (mouse) recovery of parent compound after 1h (%) |
|---|---|---|---|---|
| Shu et al. | [—C(CH₃)₂—C(=O)—OH group] | H | 100[a] | 0 |

TABLE 2-continued

*in vitro* ADME-properties of selected compounds.

| Compound | $R_1$ | $R_2$ | Microsomal stability (mouse) recovery of parent compound after 30 min (%) | Plasma stability (mouse) recovery of parent compound after 1h (%) |
|---|---|---|---|---|
| 36 | ![structure with OH and C=O] | Br | 100 | 19 ± 1 |
| Cheng et al. | ![structure with O-butyl and C=O] | H | 0 | 37 ± 4 |
| 40 | ![structure with O-butyl and C=O] | Br | 23 ± 7 | 87 ± 4 |

(a) Value was obtained using linear interpolation

REFERENCES

1. Li M, Hou Y, Wang J, Chen X, Shao Z M, Yin X M. Kinetics Comparisons of Mammalian Atg4 Homologues Indicate Selective Preferences toward Diverse Atg8 Substrates. *J Biol. Chem.* 2011; 286(9):7327-7338.
2. Apel A, Herr I, Schwarz H, Rodemann H P, Mayer A. Blocked autophagy sensitizes resistant carcinoma cells to radiation therapy. *Cancer Res.* 2008; 68(5):1485-1494.
3. Akin D, Wang S K, Habibzadegah-Tari P, et al. A novel ATG4B antagonist inhibits autophagy and has a negative impact on osteosarcoma tumors. *Autophagy* 2014; 10(11): 2021-2035.
4. Rothe K, Lin H, Lin K B L, et al. The core autophagy protein ATG4B is a potential biomarker and therapeutic target in CML stem/progenitor cells. *Blood* 2014; 123 (23):3622-3634.
5. Shu C-W, Madiraju C, Zhai D, et al. High-throughput fluorescence assay for small-molecule inhibitors of autophagins/Atg4. *J. Biomol. Screen.* 2011; 16:174-182.
6. Ketteler R, Seed B. Quantitation of autophagy by luciferase release assay. *Autophagy.* 2008; 4(6):801-806.
7. Shu C-W, Drag M, Bekes M, Zhai D, Salvesen G S, Reed J C. Synthetic substrates for measuring activity of autophagy proteases: autophagins (Atg4). *Autophagy* 2010; 6(7):936-947.

The invention claimed is:

1. A compound of Formula I or a stereoisomer, tautomer, salt, hydrate, or solvate thereof,

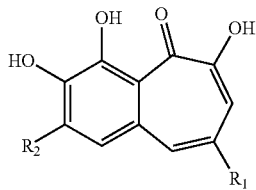

I wherein:

$R_1$ is selected from —$C_{1-6}$ alkyl, —$Ar_1$, —(C=O)—O—$R_3$ and —(C=O)—$NR_4R_5$;

$R_2$ is -halo;

$R_3$ is selected from —H and —$C_{1-8}$ alkyl;

$R_4$ and $R_5$ are each independently selected from —H, —$C_{1-8}$ alkyl, —$Ar_2$ and —$Het_1$; wherein said —$C_{1-8}$ alkyl is optionally substituted with one or more substituents —$Ar_2$;

$Ar_1$ and $Ar_2$ are each independently a 5- to 10-membered aromatic cycle; wherein each of said —$Ar_1$ and —$Ar_2$ is optionally substituted with one or more substituents selected from; -halo, —$C_{1-6}$ alkyl, and —O—$C_{1-6}$ alkyl; wherein said —$C_{1-6}$ alkyl may be optionally substituted with from one to three -halo;

$Het_1$ is a 5- to 10-membered aromatic or non-aromatic heterocycle, comprising 1 to 3 N, O or S atoms; wherein said $Het_1$ is optionally substituted with one or more substituents selected from -halo, —$C_{1-6}$ alkyl, —O—$C_{1-6}$ alkyl; wherein said —$C_{1-6}$ alkyl may be optionally substituted with from one to three -halo; and wherein said compound is not

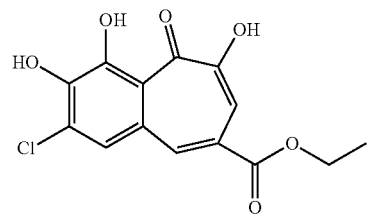

2. The compound of claim 1, wherein said compound is a compound of formula Ia;

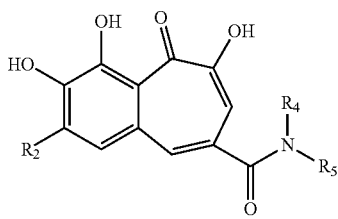

Ia wherein
R₂ is -halo;
R₄ and R₅ are each independently selected from —H, —$C_{1-8}$ alkyl, —Ar₂ and —Het₁; wherein said —$C_{1-8}$alkyl is optionally substituted with one or more substituents selected from —Ar₂;
Ar₂ is a 5- to 10-membered aromatic cycle; wherein said —Ar₂ is optionally substituted with one or more substituents selected from; -halo, —$C_{1-6}$ alkyl, and —O—$C_{1-6}$ alkyl; wherein said —$C_{1-6}$ alkyl may be optionally substituted with from one to three -halo.
Het₁ is a 5- to 10-membered aromatic or non-aromatic heterocycle, comprising 1 to 3 N, O or S atoms; wherein said Het₁ is optionally substituted with one or more substituents selected from -halo, —$C_{1-6}$ alkyl, —O—$C_{1-6}$ alkyl; wherein said —$C_{1-6}$ alkyl may be optionally substituted with from one to three -halo.

3. The compound of claim 1, wherein
R₂ is -halo; and
R₄ and R₅ are each independently selected from —H, —$C_{1-8}$ alkyl and -phenyl.

4. The compound of claim 1, wherein said compound is a compound of formula Ib;

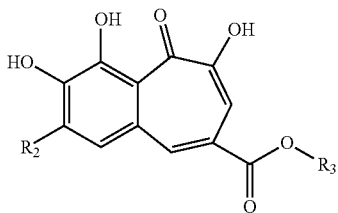

Ib wherein
R₂ is -halo; and
R₃ is selected from —H and —$C_{1-8}$ alkyl; and wherein said compound is not

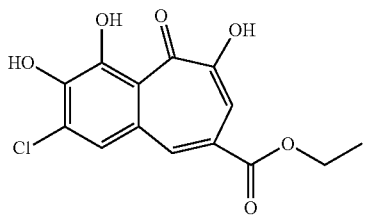

5. The compound of claim 1, wherein
R₁ is —(C=O)—O—R₃;
R₂ is -halo; and
R₃ is selected from —H and —$C_{3-8}$ alkyl.

6. The compound of claim 1, wherein R₂ is selected from the group consisting of —Cl, —F, and —Br.

7. The compound of claim 1, wherein said compound is selected from the group consisting of:

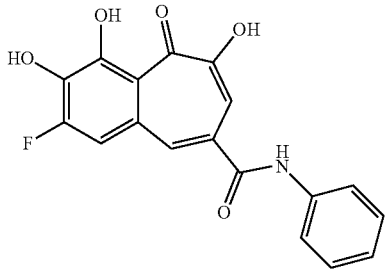

29

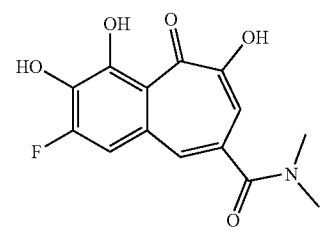

30

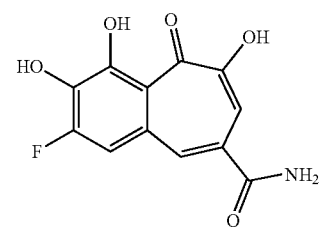

31

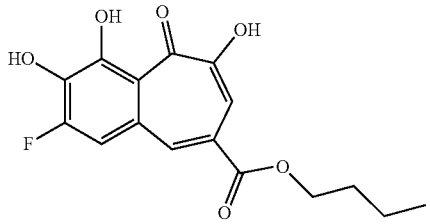

32

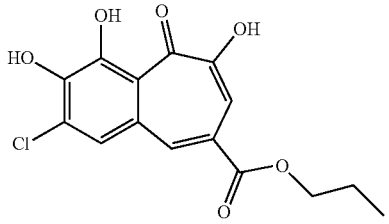

33

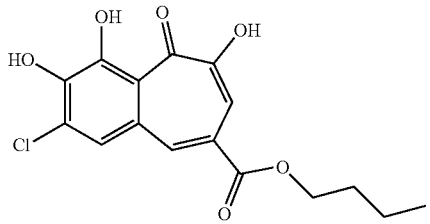

34

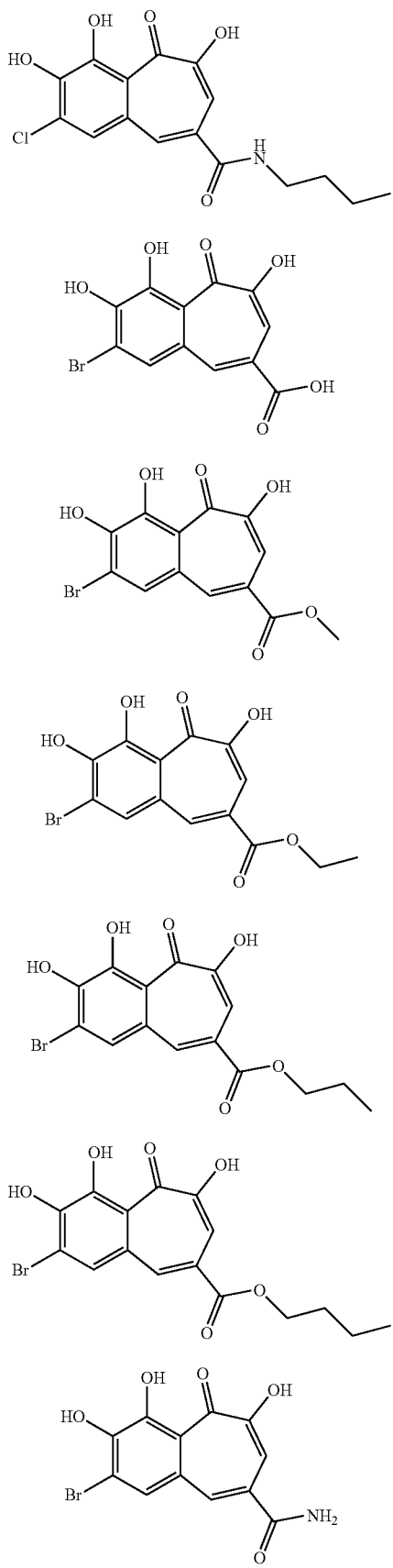
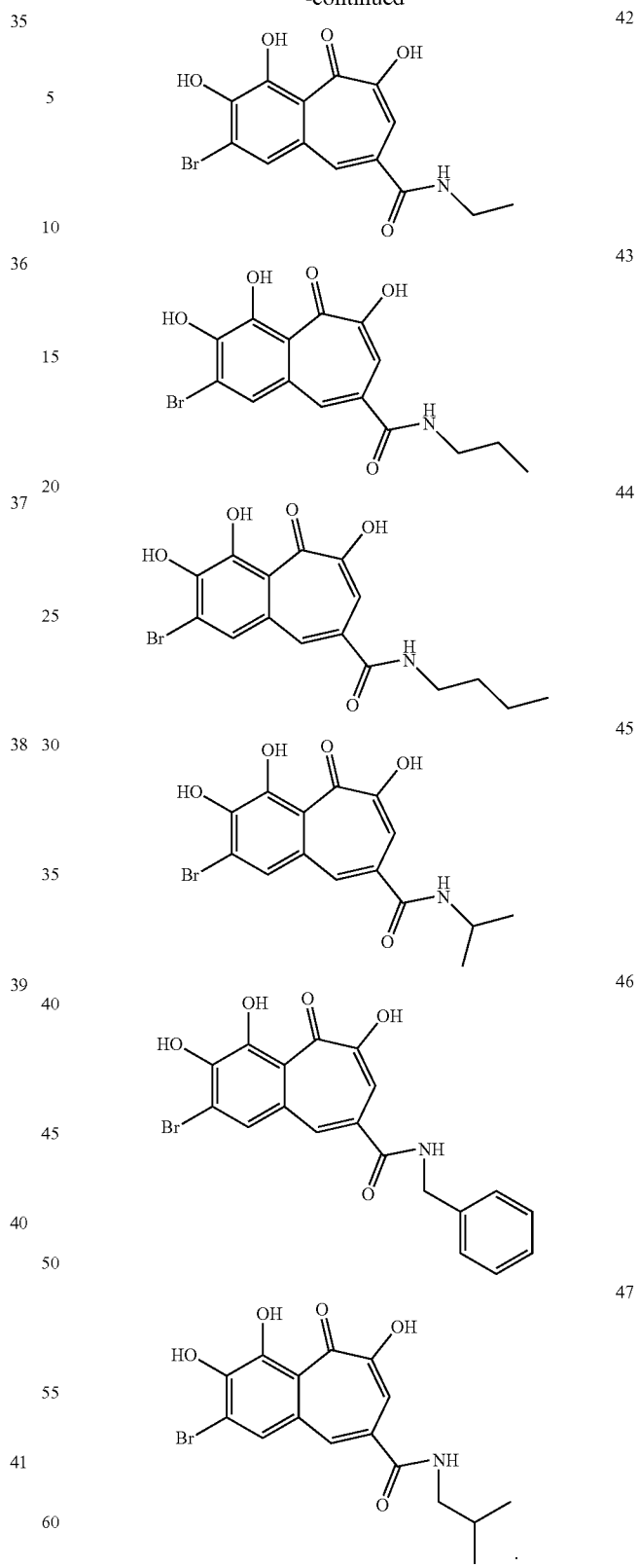
8. A method for inhibiting cysteine protease Atg4B activity, the method comprising administering to a subject an inhibitory amount of a compound of Formula I or a stereoisomer, tautomer, salt, hydrate, or solvate thereof,

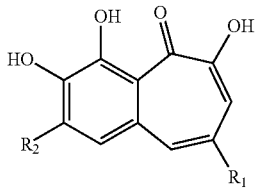

wherein:

R₁ is selected from —$C_{1-6}$ alkyl, —$Ar_1$, —(C=O)—O—$R_3$ and —(C=O)—$NR_4R_5$;

R₂ is -halo;

R₃ is selected from —H and —$C_{1-8}$ alkyl;

R₄ and R₅ are each independently selected from —H, —$C_{1-8}$ alkyl, —$Ar_2$ and —$Het_1$; wherein said —$C_{1-8}$ alkyl is optionally substituted with one or more substituents selected from —$Ar_2$;

$Ar_1$ and $Ar_2$ are each independently a 5- to 10-membered aromatic cycle; wherein each of said —$Ar_1$ and —$Ar_2$ is optionally substituted with one or more substituents selected from; -halo, —$C_{1-6}$ alkyl, and —O—$C_{1-6}$ alkyl; wherein said —$C_{1-6}$ alkyl may be optionally substituted with from one to three -halo;

$Het_1$ is a 5- to 10-membered aromatic or non-aromatic heterocycle, comprising 1 to 3 N, O or S atoms; wherein said $Het_1$ is optionally substituted with one or more substituents selected from -halo, —$C_{1-6}$ alkyl, —O—$C_{1-6}$ alkyl; wherein said —$C_{1-6}$ alkyl may be optionally substituted with from one to three -halo.

9. A pharmaceutical composition comprising a compound according to claim 1 and a pharmaceutically acceptable carrier.

* * * * *